(12) United States Patent
Griffiths et al.

(10) Patent No.: US 6,593,081 B1
(45) Date of Patent: *Jul. 15, 2003

(54) PRODUCTION OF ANTI-SELF ANTIBODIES FROM ANTIBODY SEGMENT REPERTOIRES AND DISPLAYED ON PHAGE

(75) Inventors: Andrew David Griffiths, Cambridge (GB); Hendricus Renerus Jacobus Mattheus Hoogenboom, Cambridge (GB); James David Marks, Kensington, CA (US); John McCafferty, Babraham (GB); Gregory Paul Winter, Cambridge (GB); Geoffrey Walter Grigg, Linley Point (AU)

(73) Assignees: Medical Research Council, London (GB); Cambridge Antibody Technology Limited, Cambridgeshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/532,840

(22) Filed: Mar. 21, 2000

Related U.S. Application Data

(63) Continuation of application No. 09/197,221, filed on Nov. 20, 1998, which is a continuation of application No. 08/244,597, filed as application No. PCT/GB92/02240 on Dec. 2, 1992, now Pat. No. 5,885,793.

(30) Foreign Application Priority Data

| Dec. 2, 1991 | (GB) | 9125579 |
| Dec. 2, 1991 | (GB) | 9125582 |
| Mar. 24, 1992 | (GB) | 9206318 |
| Sep. 23, 1992 | (GB) | 9206372 |

(51) Int. Cl.$^7$ .............. C12O 1/70; C12N 15/00; C07K 16/00

(52) U.S. Cl. ............... 435/5; 435/6; 435/69.1; 435/69.7; 435/320.1; 435/DIG. 1; 435/DIG. 4; 435/DIG. 14; 435/DIG. 15; 435/DIG. 47; 435/DIG. 37; 530/387.1; 530/387.3; 536/23.1; 536/23.4; 536/23.53

(58) Field of Search .............. 435/5, 6, 69.1, 435/69.7, 69.8, 91.1, 235.1, 320.1, DIG. 1, DIG. 2, DIG. 4, DIG. 34, DIG. 37, DIG. 47, DIG. 14, DIG. 15; 530/387.1, 387.3, 867; 536/23.1, 23.4, 23.53

(56) References Cited

U.S. PATENT DOCUMENTS

| 4,816,397 A | 3/1989 | Boss et al. ............ 435/68 |
| 4,946,778 A | 8/1990 | Ladner et al. ......... 435/69.6 |
| 5,091,513 A | 2/1992 | Huston et al. ......... 424/85.8 |
| 5,223,409 A | 6/1993 | Ladner et al. ......... 435/69.7 |
| 5,258,289 A | 11/1993 | Davis et al. .......... 435/69.6 |
| 5,427,908 A * | 6/1995 | Dower et al. .......... 435/5 |
| 5,567,610 A | 10/1996 | Borrebaeck et al. .... 435/240.2 |
| 5,580,717 A | 12/1996 | Dower et al. .......... 435/5 |
| 5,698,426 A | 12/1997 | Huse ................. 435/172.3 |
| 5,780,225 A | 7/1998 | Wigler et al. ......... 435/6 |
| 5,814,476 A | 9/1998 | Kauffman et al. ....... 435/69.1 |
| 5,837,500 A | 11/1998 | Lader et al. .......... 435/69.7 |
| 5,840,479 A | 11/1998 | Little et al. ......... 435/5 |
| 5,855,885 A | 1/1999 | Smith et al. .......... 424/130.1 |
| 5,885,793 A * | 3/1999 | Griffiths et al. ...... 435/69.1 |
| 5,935,823 A | 8/1999 | Fowlkes et al. ........ 435/69.7 |
| 5,948,635 A | 9/1999 | Kay et al. ............ 435/69.1 |
| 5,955,358 A | 9/1999 | Huse ................. 435/328 |
| 5,994,510 A | 11/1999 | Adair et al. .......... 530/387.3 |

FOREIGN PATENT DOCUMENTS

| AU | 27617/88 B | 7/1989 |
| EP | 0 239 400 | 9/1987 |
| EP | 0 324 162 | 12/1988 |
| EP | 368684 | 5/1990 |
| GB | 2188638 B | 5/1990 |
| GB | 91/25579.4 | 12/1991 |
| GB | 91/25582.8 | 12/1991 |
| WO | 88/06630 | 9/1988 |
| WO | 88/09344 | 12/1988 |
| WO | 90/02809 | 3/1990 |
| WO | 90/05144 | 5/1990 |
| WO | 90/14424 | 11/1990 |
| WO | 90/14430 | 11/1990 |
| WO | 90/14443 | 11/1990 |
| WO | 91/02078 | 2/1991 |
| WO | 91/10737 | 7/1991 |

(List continued on next page.)

OTHER PUBLICATIONS

Hoermann, et al., $T_3$ releasing activity by Graves' sera from Graves' thyroid in vitro, Acta Endocrinologica, 1986, 111:487–493.

(List continued on next page.)

*Primary Examiner*—Padmashri Ponnaluri
(74) *Attorney, Agent, or Firm*—Katten Muchin Zavis Rosenman

(57) ABSTRACT

Methods are disclosed for the production of human self-antibodies and antibody fragments, which bind human antigens. Methods comprise providing a library of replicable genetic display packages (rgdps), such as filamentous phage, each rgdp displaying at its surface a member of a specific binding pair which is an antibody or antibody fragment, and each rgdp containing nucleic acid sequence derived from a species of mammal. The nucleic acid sequence in each rgdp encodes a polypeptide chain which is a component part of the sbp member displayed at the surface of that rgdp. Human antibodies or antibody fragments are selected by binding with human antigens. The displayed antibody fragments may be scFv, Fd, Fab or any other fragment which has the capability of binding to and is a human antigen. Nucleic acid libraries used may be derived from V-gene sequences of unimmunised humans. Part or all of the nucleic acid may be derived from oligonucleotide synthesis.

8 Claims, 5 Drawing Sheets

FOREIGN PATENT DOCUMENTS

| WO | 91/17271 | 11/1991 |
|---|---|---|
| WO | 92/01047 | 1/1992 |
| WO | 92/06204 | 4/1992 |
| WO | 92/09690 | 6/1992 |
| WO | 92/18619 | 10/1992 |
| WO | 92/20791 | 11/1992 |
| WO | 93/03151 | 2/1993 |
| WO | 93/06213 | 4/1993 |
| WO | 93/11236 | 6/1993 |
| WO | WO 97/083200 | 3/1997 |

OTHER PUBLICATIONS

Hoogenboom et al., "Building Antibodies From Their Genes", *Immunol. Rev.*, vol. 130 pp. 41–68 (1992).

Larrick et al., "Recombinant Antibodies", *Hum. Antibod. Hybridomas*, vol. 2, pp. 172–189 (1991).

Wallukar, G., et al., "Autoantikörper gegen den $\beta_1$–adrenergen Rezeptor bei Myokarditis und dilatativer Kardiomyopathie: Lokalisation von zwei Epitopen", *Z. Kardiol*, 81:Suppl. 4, 79–83 (1992).

Complaint, filed Apr. 23, 1999; (5 pages) Morphosys AG v Cambridge Antibody Limited, Case No. 1:99CV01012; Judge James Robertson.

First Amended Complaint filed May 6, 1999–(18 pages) Morphosys AG v Cambridge Antibody Limited, Case No. 1:99CV01012; Judge James Robertson.

Defendant Cambridge Antibody Technology, Limited's Motion to Dismiss Plaintiff MorPhosys AG's Complaint filed Jun. 08, 1999. (4 pages) Morphosys AG v Cambridge Antibody Limited, Case No. 1:99CV01012; Judge James Robertson.

Response of Plaintiff MorphoSys AG to Cambridge Antibody Technology Ltd.'s First Set of Interrogatories and Request for Production of Documents and Things filed Oct. 18, 1999–(20 pages) Morphosys AG v Cambridge Antibody Limited, Case No. 1:99CV01012; Judge J. Robertson.

Plaintiff's Supplemental Answer to Interrogatory No. 2. (9 pages) Morphosys AG v Cambridge Antibody Limited, Case No. 1:99CV01012; Judge James Robertson.

Response of Plaintiff Morphosys AG to Cambridge Antibody Technology Ltd's First Set of Interrogatories and Request for Production of Documents and Things filed Mar. 27, 2000 (19 pages) Morphosys AG v Cambridge Antibody Limited, Case No. 1:99CV01012; Judge J. Robertson.

Response of Plaintiff Morphosys AG to Cambridge Antibody Technology Ltd's Second Set of Interrogatories filed Jul. 3, 2000 (3 pages) Morphosys AG v Cambridge Antibody Limited, Case No. 1:99CV01012; Judge James Robertson.

Response of MorphoSys AG to Cambridge Antibody Technology's Third Set of Interrogatories filed Aug. 14, 2000 (4 pages) Morphosys AG v Cambridge Antibody Limited, Case No. 1:99CV01012; Judge James Robertson.

Declaration of Edward S. Golub, Ph.D. In Support of MorphoSys' Motion for Partial Summary Judgment of Non-infringement filed Sep. 1, 2000–(6 pages) Morphosys AG v Cambridge Antibody Limited, Case No. 1:99CV01012; Judge James Robertson.

Edward S. Golub, Ph.D. Curriculum Vitae (12 pages) Morphosys AG v Cambridge Antibody Limited, Case No. 1:99CV01012; Judge James Robertson.

Expert Report of Edward S. Golub, Ph.D. dates Jun. 2000 (with Exhibit 1 E. S. Golub Curriculum Vitae Exhibit 2 E. S. Golub Validity Report and Exhibit 3 Declaration of E.S. Golub regarding Immunological concepts) (53 pages) Morphosys AG v Cambridge Antibody Limited, Case No. 1:99CV01012; Judge J. Robertson.

Rebuttal Expert Report of Edward S. Golub, Ph.D. (8 pages) Morphosys AG v Cambridge Antibody Limited, Case No. 1:99CV01012; Judge James Robertson.

Reply of Edward S. Golub, Ph.D. to Rebuttal Expert Reports of Edward P. Cohen, M.D. and Ronald H. Jackson, P.D., dated Aug. 1, 2000 (5 pages) Morphosys AG v Cambridge Antibody Limited, Case No. 1:99CV01012; Judge James Robertson.

Declaration of Carlos F. Barbas III, Ph.D. in Support of MorphoSys' Motion for Partial Summary Judgment of Non-infringement filed Sep. 1, 2000 –(3 pages) Morphosys AG v Cambridge Antibody Limited, Case No. 1:99CV01012; Judge James Robertson.

Carlos F. Barbas III, Ph.D. Cirruculum Vitae (16 pages) Morphosys AG v Cambridge Antibody Limited, Case No. 1:99CV01012; Judge James Robertson.

Trial Transcript –Edward Golub, Ph.D. –Mar. 21, 2001– Civil Action No. 99–1012 JR (pp. 623–637) Morphosys AG v Cambridge Antibody Limited, Case No. 1:99CV01012; Judge James Robertson.

Trial Transcript –Edward Golub, Ph.D. –Mar. 22, 2001– Civil Action No. 99–1012 JR (a.m. Session) (pp. 638–689) Morphosys AG v Cambridge Antibody Limited, Case No. 1:99CV01012; Judge James Robertson.

Trial Transcript –Edward Golub, Ph.D. –Mar. 22, 2001– Civil Action No. 99–1012 (p.m. session) ( pp. 698–721) Morphosys AG v Cambridge Antibody Limited, Case No. 1:99CV01012; Judge James Robertson.

Trial Transcript –Carlos Barbas, Ph.D. –Mar. 22, 2001– Civil Action No. 99–1012 (pp. 766–777) Morphosys AG v Cambridge Antibody Limited, Case No. 1:99CV01012; Judge James Robertson.

Trial Transcript –Carlos Barbas, Ph.D. –Mar. 26, 2001– Civil Action No. 99–1012 (a.m. session) (pp. 790–878). Morphosys AG v Cambridge Antibody Limited, Case No. 1:99CV01012; Judge James Robertson.

Trial Transcript –Carlos Barbas, Ph.D. –Mar. 26, 2001– Civil Action No. 99–1012 (p.m. session) (pp. 883–911) Morphosys AG v Cambridge Antibody Limited, Case No. 1:99CV01012; Judge James Robertson.

Trial Transcript, Closing Arguments of Attorney Hart, Mar. 28, 2001 (pp. 1306–1312). Morphosys AG v Cambridge Antibody Limited, Case No. 1:99CV01012; Judge James Robertson.

Expert Report of Ronald Jackson, Ph.D., Dated Aug. 11, 2000 (20 Pages) Morphosys AG v Cambridge Antibody Limited, Case No. 1:99CV01012; Judge James Robertson.

Expert Report of Edward S. Cohen, Dated Jun. 25, 2000, (37 pages), Morphosys AG v Cambridge Antibody Limited, Case No. 1:99CV01012; Judge James Robertson.

Expert Rebuttal Report of Edward S. Cohen, Jul. 26, 2000, (13 pages), Morphosys AG v Cambridge Antibody Limited, Case No. 1:99CV01012; Judge James Robertson.

Bachman et al., "Absence of co–stimulation and not the Intensity of TCR signaling is critical for the induction of T cell unresponsiveness in vivo", *Eur. J. Immunol.*, 1999.29:pp. 2156–2166.

Batteaux. et al., "Transgenic Expression of Fas Ligand on Thyroid Follicular Cells Prevents Autoimmune Thyroiditis", *J. of Immunology*, 2000, 164: 1681–1688.

Better, et al., "*Escherichia coli* Secretion of an Active Chimeric Antibody Fragment", *Science*, 240:1041–1043.

Breitling, et al., "A surface Expression Vector or antibody screening", *Gene*, 104 (1991), pp. 147–153.

Bruin, et al., "Neutrophil Antibody Specificity in Different Types of Childhood Autoimmune Neutropenia", *Blood*, No. 5, (Sep. 1) 1999, pp. 1797–1802.

Chen, et al., "A testicular antigen abberrantly expressed in human cancers detected by autologous antibody Screening", *PNAS USA*, vol. 94, pp. 1914–1918, Mar. 1997 Immunology.

Choudhury, et al., "Disruption of T Cell Tolerance to Self–Immunoglobulin Causes Polyclonal B Cell Stimulation Followed by Inactivation of Responding Autoreactive T Cells", *The Journal of Immunology*, 2000, 164: pp. 1713–1721.

Glockshuber, et al., "A Comparison of Strategies to Stabilize Immunoglobulin $F_v$ Fragments", *Biochem.*, 29:1362–1367.

Gure et al., "SSX: A Multigene Family With Several Members Several Members Transcribed in Normal Tests and Human Cancer", *Int. J. Cancer*, 72:965–971, (1997).

Janeway, et al., "The interaction f the antibody molecule with specific antigen", Chapter 3, *Immunology*, CB Publications, (1999), pp. 86–93.

Janeway, et al., "Selection of B cells" Chapter 6, *Immunology*, CB Publications, (1999), pp. 209–213.

Janeway, et al., "Tolerance and loss of tolerance to self tissues", Chapter 13, *Immunology*, CB Publications, (1999), pp. 520–532.

Knappik, et al., "Fully Synthetic Combinatorial Antibody Libraries (HuCal) Based on Modular Consensus Frameworks and CDRs Randomized with Trinuclotides", *J. Mol. Biol.*, (2000) 200:pp. 57–86.

Kotera, et al., "Humoral Immunity Against a Tandem Repeat Epitope of Human Mucin MUC–1 in Sera from Breast, Pancreatic, and Colon Cancer Patients", *Cancer Res.*, 54, 2856–2860.

Kuo, et al., "Crossreactive B cells are present during a primary but not secondary response in BALB/c mice expressing a bcl–2 transgene", "*Molecular Immunology*", 36 (1999) pp. 471–479.

Kuwahara, et al., "Autoantibody against Testosterone in a woman with Hypergonadotropic Hypogonadism", *J. Clin. Endocrin. & Metabolism*, vol. 85, pp. 14–16.

Maxwell, et al., "Danger and OX40 Receptor Signaling Synergize to Enhance Memory T Cell Survival by Inhibiting Peripheral Deletion", *J. Immunology*, 2000. 164: pp. 107–112.

Morgan, et al., "Antigen Concentration and Precursor Frequency Determine the Rate of $CD8^+T$ Cell Tolerance to Peripherally Expressed Antigens", *J. of Immunology*, 163:pp. 723–727.

Oosterwegel, et al., "CTLA–4 and T Cell activation", *Current Opinion in Immunology*, 1999, pp. 294–300.

Dr. Noel Rose, "The Uses of AutoAntibodies", in Peter & Schoefeld, *AutoAntibodies* at xxvii (1996).

Sahin et al., "Human neoplasms elicit multiple specific Immune response in the autologous host", *PNAS USA* vol. 92, pp. 11810–11813, Dec. 1995.

Sahin et al., "Serological identification of human tumor antigens", *Cancer*, 709–716.

Sakaguchi, et al., "Regulatory T Cells Key Controllers of Immunologic Self–Tolerance", *Cell*, pp. 455–458.

Scanlan, et al., "Characterization of Human Colon Cancer Antigens Recognized by Autologous Antibodies", *Int. J. Cancer*, 76:652–658 (1998).

Skerra, et al., "Assembly of a Functional Immunoglobulin $F_v$ Fragment in *Escherichia coli*", *Science*, vol. 240, pp. 1038–1041.

Türeci, et al., "Molecular Definition of a Novel Human Galectin Which is Immumogenic in Patients with Hodgkins Disease", *J. of Biol. Chem.*, vol. 272, No. 10, Mar. 7, 1997, pp. 6416–6422.

Türeci, et al., "Identification of a meiosis–specific protein as a member of the class of cancer/testis antigens", *PNAS USA*, vol. 95:pp. 5211–5216, Apr. 1998, Immunology.

Türeci, et al., "Human carbonic anhydrase XII: cDNA cloning, expression, and chromosal localization of a carbonic anhydrase gene that is overexpressed in some renal cell cancers", *PNAS USA*, vol. 95, pp. 7608–7613, Jun. 1998.

Alzari et al., "Three Dimensional Structure Determination of an Anti–2–Phenyloxazolone Antibody: The Role of Somatic Mutation and Heavy–Light Chain Pairing in the Maturation of an Immune Response," *EMBO J.*, 9:3807–3814 (1990).

Amit et al., "Three–Dimentional Structure of an Antigen–Antibody Complex at 2.8 Å Resolution," *Science*, 233:747–753 (1986).

Avrameas, "Natural autoantibodies: from 'horror autotoxicus' to 'gnothis seauton'", *Immunology Today*, 12:154–159 (1991).

Bass et al., "Hormone Phage; An Enrichment Method for Variant Proteins With Altered Binding Properties", *Proteins, Structure, Function and Genetics*, 8:309–314 (1990).

Bendtzen et al., "Autoantibodies to cytokines—friends or foes?", *Immunology Today*, 11(5):167–179 (1999).

Bentley et al., "Human Immunoglobulin Variable Region Genes–DNA Sequences of Two $V_K$ Genes and a Pseudogene," *Nature*, 288:730–3 (1980).

Berman et al., "Content and Organization of the Human Ig $V_H$ Locus: Definition of Three New $V_H$ Families and Linkage to the Ig $C_H$ Locus," *EMBO J*, 7:727–738 (1988).

Bernard et al., "Genomic Sequence of IGLV1S2, A Human Immunoglobulin Variable Lambda Gene Belonging to Subgroup I," *Nucleic Acids Res*, 18:7139 (1990).

Bird et al., "Single–Chain Antigen–Binding Proteins," *Science*, 242:423–426 (1988).

Bouanani, M. et al., "Autoimmunity to Human Thyroglobulin," *Arthritis and Rheumatism*, 34(12):1585–1593 (Dec., 1991).

Brockly et al., "First Nucleotide Sequence of a Human Immunoglobulin Variable λ Gene Belonging to Subgroup II," *Nucleic Acids Res*, 17:3976 (1989).

Carter et al., "Improved Oligonucleotide Site–Directed Mutagenesis Using M13 Vectors," *Nucl. Acids Res.*, 13:4431–4443 (1985).

Casali, et al., "Probing the Human B–Cell Repertoire With EBV: Polyreactive Antibodies and $CD5^+$ B Lymphocytes [1,2]," *Ann. Rev. Immunol.*, 7:513–535 (1989).

Chen et al., "A 16/6 Idiotype–Positive Anti–DNA Antibody Is Encoded By a Conserved $V_H$ Gene With No Somatic Mutation," *Arthritis Rheum*, 31:1429–1431 (1988).

Chothia et al., "Canonical Structures for the Hypervariable Regions of Immunoglobulins," *J. Mol. Biol.*, 196:901–917 (1987).

Chothia et al., "Conformation of Immunoglobulin Hypervariable Regions," Nature, 342:877–893 (1989).

Chothia et al., "Structural Repertoire of the Human $V_H$ Segments," J. Mol. Biol., 227:779–817 (1992).

Clackson et al., "Making Antibody Fragments Using Phage Display Libraries," Nature, 352:624–628 (1991).

Cohen et al., "Natural Autoantibodies Might Prevent Autoimmune Disease," Immunol. Today, 7:363–364 (1986).

Cunningham et al., "Antibody engineering—how to be human," Trends Biotechnol (England), 10 (4):112–3 (Apr., 1992).

Curti, "Physical barriers to drug delivery in tumors," Crit. Rev. Oncol. Hematol., (Ireland), 14 (1):29–39 (Feb., 1993).

Daley et al., "Molecular Characterization of the Human Immunoglobulin VλI Germline Gene Repertoire," Molecular Immunology, 29:1031–1042 (1992).

Davis et al., "Antibody and HIV–1 gp120 Recognition of CD4 Undermines the Concept of Mimicry Between Antibodies and Receptors," Nature, 358:76–79 (1992).

de la Cruz et al., "Immumogenicity and Epitope Mapping of Foreign Sequences via Genetically Engineered Filamentous Phage", J. Biol. Chem., 263(9):4318–4322 (1988).

DeBellis et al., "Regulated Expression of Foreign Genes Fused to lac: Control by Glucose Levels in Growth Medium," Nucl. Acids Res., 18:1311 (1990).

Dejana et al., "Modulation of Endothelial Cell Functions by Different Molecular Species of Interleukin 1," Blood, 69:695–699 (1987).

Dillman et al., "Monoclonal antibodies for treating cancer," Ann Intern Med (United States,) 111 (7):592–603 (Oct., 1989).

Ditzel et al., "The nature of the autoimmune antibody repertoire in human immunodeficiency virus type 1 infection", Proc. Natl. Acad. Sci. USA, 91:3710–3714 (1994).

Dower et al., "Retention of Ligand Binding Activity by the Extracellular Domain of the IL–1 Receptor," J. Immunol., 142:4314–4320 (1989).

Eisen, H.N., "Determination of Antibody Affinity for Haptens and Antigens by Means of Fluorescence Quenching," Meth. Med. Research, 10:115–121 (1964).

Embleton et al., "In–Cell PCR from mRNA: Amplifying and Linking the Rearranged Immunoglobulin Heavy And Light Chain V–Genes Within Single Cells," Nucleic Acids Research, 20:3831–3837 (1992).

Foote et al., "Kinetic Maturation of an Immune Response," Nature, 352:530–532 (1991).

Frippiat et al., "First Genomic Sequence of a Human Ig Variable Lambda Gene Belonging to Subgoup III," Nucleic Acids Research, 18:7134 (1990).

Gaulton et al., "Idiotypic Mimicry of Biological Receptors" Ann. Rev. Immunol., 4:253–280 (1986).

Gearing et al., "A Simple Sensitive Bioassay for Interleukin–1 Which is Unresponsive to $10^3$ U/ml of Interleukin–2," J. Immunol. Methods, 99:7–11 (1987).

Gendler et al., "A Highly Immunogenic Region of a Human Polymorphic Epithelial Mucin Expressed by Carcinomas Is Made Up of Tandem Repeats," J. Biol. Chem., 263:12820–12823 (1988).

Gheradi et al., "A Single–Step Procedure for Cloning and Selection of Antibody–Secreting Hybridomas," J. Immunol. Meth., 126:61–68 (1990).

Goldsten,G., "Overview of the development of Orthoclone OKT3: monoclonal antibody for therapeutic use in tranplantation," Transplant Proc (United States), 19 (2 Suppl 1): 1–6 (Apr., 1987).

Goodnow et al., "Altered Immunoglobulin Expression and Functional Silencing of Self–Reactive B Lymphocytes in Transgenic Mice," Nature, 334:676–682 (1988).

Gorick et al., "Three Epitopes on the Human Rh Antigen D Recognized by $^{125}$I–Labelled Human Monoclonal IgG Antibodies," Vox. Sang., 55:165–170 (1988).

Guarante, L. et al., "Technique for Expressing Eukaryotic Genes in Bacteria," Biotechnology (United States), 24:261–3 (1992).

Gum et al., "Molecular Cloning of cDNAs Derived from a Novel Human Intestinal Mucin Gene," Biochemical Biophysical Research Commun., 171:407–415 (1990).

Güssow et al., "Direct Clone Characterization from Plaques and Colonies by the Polymerase Chain Reaction," Nucleic Acids Research, 17:4000 (1989).

Harris et al., "Therapeutic antibodies—the coming of age," Trends Biotechnol (England), 11(2):42–4 (Feb., 1993).

Hartley et al., "Elimination from Peripheral Lymphoid Tissues of Self–Reactive B Lymphoctyes Recognizing Membrane–Bound Antigens," Nature, 353:765–769 (1991).

Hassan et al., "Prevalence of anti–Fab antibodies in patients with autoimmune and infectious diseases", Clin. exp. Immunol. 89:423–426 (1992).

Hawkins et al., "Selection of Phage Antibodies by Binding Affinity," J. Mol. Biol., 226:889–896 (1992).

Hird et al., in: Genes and Cancer, Chapter 17 (1990).

Holmberg et al., "Natural Antibodies and Autoimmunity," Immunol. Today, 6:356–357 (1985).

Hoogenboom et al., "Multi–Subunit Proteins on the Surface of Filamentous Phage: Methodologies for Displaying Antibody (Fab) Heavy and Light Chains," Nucleic Acids Research, 19:4133–4137 (1991).

Huse et al., "Generation of a Large Combinatorial Library of the Immunoglobulin Repertoire in Phage Lambda", Science, 246:1275–1281 (1989).

Huston et al., "Protein Engineering of Antibody Sites: Recovery of Specific Activity in an Anti–Digoxin Single–Chain Fv Analogue Produced in Escherichia coli," Proc. Natl. Acad. Sci., USA 85:5879–5883 (1988).

Ichihara et al., "Organization of Human Immunoglobulin Heavy Chain Diversity Gene Loci," Embo J., 7:4141–4150 (1988).

International Search Report, PCT/GB92/02240.

Jönsson et al., "Real Time Biospecific InterationAnalysis: The Integration of Surface Plasmon Resonance Detection, General Biospecific Interface Chemistry and Microfluidics into One Analytical System," In: Real Time Biospecific Interaction, A. Turner (Ed.), JAI Press Ltd., San Diego, vol. 2, pp. 291–336 (1992).

Jönsson et al., "Real–Time Biospecific Interaction Analysis Using Surface Plasmon Resonance and a Sensor Chip Technology," Biotechniques, 11: 620–627 (Nov., 1991).

James, K. et al., "Human monoclonal antibody production: Current status and future prospects," J. Immunological Methods, 100:5–40 (1987).

Jerome et al., "Adenocarcinoma Reactive Cytotoxic T Lymphocytes Recognize an Epitope Present on the Protein Core of Epithelial Mucin Molecules", Cellular Immunity and the Immunotherapy of Cancer, pp. 321–328 (1990).

Johnsson et al., "Immobilization of Proteins to a Carboxymethyldextran–Modified Gold Surface for Biospecific Interaction Analysis in Surface Plasmon Resonance Sensors," *Anal. Biochem.*, 198:268–277 (1991).

Kang et al., "Linkage of recognition and replication functions by assembling combinatorial antibody Fab libraries along phage surface", *Proc. Natl. Acad. Sci. USA*, 88:4363–4366 (1991).

Karlsson et al., "Kinetic Analysis of Monoclonal Antibody–Antigen Interactions With A New Biosensor Based Analytical System," *J. Immunol. Methods*, 145:229–240 (1991).

Kettleborough et al., "Humanization of a mouse monoclonal antibody by CDR–grafting: the importance of framework residues on loop conformation," *Protein Eng (England)*, 4(7):773–83 (Oct., 1991).

Kim, J.G and Abeyounis, C.J., "Monoclonal Rat Antibodies To Rat Carcinoembryonic Antigen," *Immunological Investigations*, 17(1):41–48 (1988).

Kim, J.G. and Abeyounis, C.J., "Isolation and Characterization of Rat Carcinoembryonic Antigen," *Int. Arch. Allergy Appl. Immunol.*, 92:43–49 (1990).

Klobeck et al., "Subgroup IV of Human Immunoglobulin K Light Chains is Encoded by a Single Germline Gene," *Nucleic Acids Research*, 13:6515–29 (1985).

Leusch et al., "Failure to demonstrate TNF α–specific autoantibodies in human sera by ELISA and Western blot", *Journal of Immunological Methods*, 139:145–147 (1991).

Lydyard et al., "The Antibody Repertoire of Early Human B Cell I. High Frequency of Autoreactivity and Polyreactivity," *Scand J. Immunol.*, 31:33–43 (1990).

Mach et al., "Statistical Determination of the Average Values of the Extinction Coefficients of Tryptophan and Tyrosine in Native Proteins," *Anal. Biochem.*, 200:74–80 (1992).

Malthiéry et al., "Primary Structure of Human Thyroglobulin Deduced from the Sequence of Its 8448–Base Complementary DNA," *Eur. J. Biochem.*, 165:491–498 (1987).

Marks et al., "By–Passing Immunization: Building High Affinity Human Antibodies by Chain Shuffling", *Bio/Technology*, 10:779–783 (1992).

Marks et al., "By–passing Immunization Human Antibodies from V–gene Libraries Displayed on Phage", *J. Mol. Biol.*, 222:581–597 (1991).

Marks et al., "Oligonucleotide Primers For Polymerase Chain Reaction Amplification of Human Immunoglobulin Variable Genes and Design of Family–Specific Oligonucleotide Probes," *Eur. J. Immunol*, 21:985–991 (1991).

Matsuda et al., "Organization of Variable Region Segments of the Human Immunoglobulin Heavy Chain: Duplication of the $D_5$ Cluster within the Locus and Interchromosomal Translocation of Variable Region Segments," *EMBO J.*, 9:2501–2506 (1990).

Matthyssens et al., "Structure and Multiplicity of Genes for the Human Immunoglobulin Heavy Chain Variable Region," *Proc Natl Acad. Sci., USA*, 77:6561–6565 (1980).

McCafferty et al., "Phage antibodies: filamentous phage displaying antibody variable domains", *Nature* 348:552–554 (1990).

Miller et al., "A Monoclonal Autoantibody That Promotes Central Nervous System Remyelination in a Model of Multiple Sclerosis is a Natural Autoantibody Encoded by Germline Immunoglobulin Genes," *J. Immunol*, 154:2460–2469 (1995).

Milstein, F.R.S., "Antibodies: a paradigm for the biology of molecular recognition", *Proc. R. Soc. London* B, 239:1–16 (1990).

Moynier et al., "The B Cell Repertoire in Rheumatoid Arthritis. I. Frequency of EBV–Indicible Circulating Precursors Producing Autoantibodies", *Journal of Autoimmunity*, 4:631–649 (1991).

Munroe et al., "An Hsp70–like Protein in the ER: Identity with the 78 kd Glucose–Regulated Protein and Immunoglobulin Heavy Chain Binding Protein," *Cell*, 46:291–300 (Jul., 1986).

Nemazee et al., "Clonal Deletion of B Lymphocytes in a Transgenic Mouse Bearing Anti–MHC Class I Antibody Genes," *Nature*, 337:562–566 (1989).

Nossal, "Immunologic Tolerance: Collaboration Between Antigen and Lymphokines", *Science*, 245:147–153 (1989).

Orencole et al., "Characterization of a Subclone (D10S) of the D10.G4.1 Helper T–Cell Line which Proliferates to Attomolar Concentrations of Interleukin–1 in the Absence of Mitogens," *Cytokine (United States )*, 1(1):14–22 (Nov., 1989).

Osband et al., "Problems in the investigational study and clinical use of cancer immunotherapy," *Immunol Today (England)*, 11 (6):193–5 (Jun., 1990).

Pargent et al., "The Human Immunoglobulin χ Locus. Characterization of the duplicated O Regions," *Eur. J. Immunol.*, 21:1821–7 (1991).

Parmley et al., "Antibody–selectable filamentous fd phage vectors: affinity purification of target genes", *Gene*, 73:305–318 (1988).

Pech et al., "Organization and Evolution of a Gene Cluster for Human Immunoglobulin Variable Regions of the Kappa Type," *J. Mol Biol*, 176:189–204 (1984).

Portolano et al., "A Human FAB Fragment Specific for Thyroid Peroxidase Generated by Cloning Thyroid Lymphocyte–Derived Immunoglobulin Genes in a Bacteriophage Lambda Library", *Biochemical and Biophysical Research Communications*, 179(1):372–377 (1991).

Price et al., "Immunological and Structural Features of the Protein Core of Human Polymorphic Epithelial Mucin," *Molec. Immunol.*, 27:795–802 (1990).

Queen et al., "A humanized antibody that binds to the interleukin 2 receptor," *Proc Natl Acad Sci U S A (United States)*, 86 (24):10029–33 (Dec., 1989).

Rath et al., "An Inhibition Enzyme Immunoassay for Estimating Relative Antibody Affinity and Affinity Heterogeneity," *J. Immunol Methods*, 106:245–249 (1988).

Riechmann et al., "Reshaping human antibodies for therapy," Nature (England), 332 (6162):323–7 (Mar., 1988).

Rossomando et al., "Studies on the Bacteroiphage fl I. Alkali–induced Disassembly of the Phage into DNA and Protein," *J. Mol. Biol.*, 36:387–399 (1968).

Russell et al., "Peripheral Deletion of Self–Reactive B Cells," *Nature*, 354:308–311 (1991).

Saiki et al., "Enzymatic Amplification of β–Globin Genomic Sequences and Restriction Site Analysis for Diagnosis of Sickle Cell Anemia," *Science*, 230:1350–1354 (1985).

Sanger et al., "DNA Sequencing With Chain–Terminating Inhibitors," *Proc Natl. Acad Sci, USA*, 74:5463–5467 (1977).

Sanz et al., "Nucleotide Sequences of Eight Human Natural Autoantibody $V_H$ Regions Reveals Apparent Restricted Use of $V_H$ Families", *The Journal of Immunology*, 142(11):4054–4061 (1989).

Sanz et al., "The Smaller Human $V^H$ Gene Families Display Remarkably Little Polymorphism," *EMBO J., 8:*3741–3748 (1989).

Scott et al., "Clonal Characterization of the Human IgG Antibody Repertoire to *Haemophilus influenzae* type b Polysaccharide," *J Immunol, 47:*4007–13 (1991).

Scott et al., "Searching for Peptide Ligands with an Epitope Library," *Science, 249:*386–390 (1990).

Sege et al., "Use of Anti–idiotypic Antibodies as Cell–Surface Receptor Probes" *Proc. Natl. Acad. Sci, USA, 75:*2443–2447 (1978).

Sekigawa et al., "Characterization of Autoantibodies to the CD4 Molecule in Human Immunodeficiency Virus Infection", *Clinical Immunology and Immunopathology,* 58:145–153 (1991).

Short et al., "λ ZAP: a bacteriophage λ expression vector with in vivo excision properties", *Nucleic Acids Research,* 16(15):7583–7600 (1988).

Sims et al., "Cloning the Interleukin 1 Receptor from Human T Cells," *Proc. Natl. Acad. Sci., USA, 86:*8946–8950 (1989).

Smith, "Filamentous Fusion Phage: Novel Expression Vectors That Display Cloned Antigens on the Virion Surface", *Science,* 228:1315–1317 (1985).

Steinman et al., "Prospects for Specific Immunotherapy in Myasthenia Gravis," *FASEB J., 4:*2726–2731 (1990).

Takii et al., "Interleuki–1 Up–Regulates Transcription of Its Own Receptor in a Human Fibroblast Cell Line TIG–1: Role of Endogenous $PGE_2$ and cAMP," *Eur. J. Immunol., 22:*1221–1227 (1992).

Tomlinson et al., "The Repertoire of Human Germline $V_H$ Sequences Reveals about Fifty Groups of $V_H$ Segments with Different Hypervariable Loops," *J. Mol. Biol., 227:*776–798 (1992).

Tsunetsugu–Yokota et al., "Expression of an immunogenic region of HIV by a filamentous bacteriophage vector", *Gene,* 99:261–265 (1991).

Waldmann TA, "Monoclonal antibodies in diagnosis and therapy," Science (United States), 252 (5013):1657–62 (Jun., 1991).

Ward et al., "Binding Activities of a Repertoire of Single Immunoglobulin Variable Domains Secreted from *Escherichia coli," Nature, 341:*544–546 (1989).

Williams et al., "The Immunoglobulin Superfamily–Domains for Cell Surface Recognition," *Ann. Rev. Immunol., 6:*381–405 (1988).

Winter et al., "Man–made antibodies", *Nature* 349:293–299 (1991).

Wraith et al., "T Cell Recognition as the Target for Immune Intervention in Autoimmune Disease," *Cell, 57:*709–715 (1989).

Yativ et al., "The Detection of Antithyroglobulin Activity in Human Serum Monoclonal Immunoglobulins (Monoclonal Gammopathies)", *Immunol. Res.,* 12:330–337 (1993).

Barbas, et al., "Assembly of combinatorial antibody libraries on phage surfaces: The gene III site", *PNAS USA,* 88:7978–7982 (1991).

Answers to Interrogatories.

Supplemental Answer to Interrogatories.

Abstract, Sioud–M. et al., "Characterization of naturally occurring autoantibodies against tumour necro is factor–alpha (TNF–alpha): in vitro function and precise epitope maping in phage epitope library", *Clin–Exp–Immunol.,* 98(3):520–525 (1994).

Abstract, Tsuchiyama–L, et al., "Comparison of anti–TNF alpha autoantibodies in plasma and from EBV transformed lymphocytes of autoimmune and normal individuals", *Human Antibodies Hybridomas,* 6(2):73–76 (1995).

Abbas et al., "Cellular and Molecular Immunology," Saunders, Third Edition, p. 412 (1997).

Alberts et al., "Molecular Biology of the Cell," Garland Publications, Third Edition, p. 96 (1994).

Avrameas and Ternynck, "Natural Antibodies," in Delves, P., and I. Roitt, *The Encyclopedia of Immunology,* Second Edition, Academic Press, pp. 1806–1809 (1998).

Barbas et al., "Combinatorial Immunoglobulin Libraries on the Surface of Phage (Phabs): Rapid Selection of Antigen Specific Fabs," Methods: Companion Methods Enzymol., 2:119 (1991).

Beidler et al., "Cloning and High Level Expression of a Chimeric Antibody with Specificity for Human Carcinoembryonic Antigen," J. Immunology, 141:4053–4060 (1988).

Berborowicz and Jaroszewski, "Carcinoembryonic Antigen as an Autoantigen," Immunol. Ser., 52:65–83 (1982).

Berzofsky et al., "Antigen–Antibody Interactions and Monoclonal Antibodies," in Paul, W., *Fundamental Immunology,* Second Edition, Chapter 12, p. 332 (see also, Fourth Edition, 1994, [1999] chapter 4, p. 91.

Boerner et al., "Production of Antigen–Specific Human Monoclonal Antibodies From In Vitro–Primed Human [Splenocytes], " J. Immunol., 147:86–95 (1991).

Breitling et al., "A Surface Expression Vector for Antibody Screening," Gene, 104:147–153 (1991).

Burton et al., "A Large Array of Human Monoclonal Antibodies to Type 1 Human Immunodeficiency Virus from Combinatorial Libraries of Asymptomatic Seropositive Individuals," Proc. Natl. Acad. Sci., 88:10134–10137 (1991).

Chang et al., "Expression of Antibody Fab Domains on Bacteriophage Surfaces: Potential Use of Antibody Selection," J. Immunol., 1047:3610–3614 (1991).

Cohen, P.L., "Systemic Autoimmunity," in Paul, W., *Fundamental Immunology,* Fourth Edition, Lippincott–Raven, p. 1608 [1067].

Delves, P.J., "Autoimmunity," in Delves, P. and I. Roitt, *The Encyclopedia of Immunology,* Second Edition, Academic Press, p. 292 (1998).

Dighiero et al., "Naturally Occurring Autoantibodies Against Nine Common Antigens in Human Sera," J. Immunol., 218[128]:2788–2792 (1982).

Fomsgaard et al. "Auto–antibodies to Tumor Necrosis Factor in Healthy Humans and Patients with Inflammatory Diseases and Gram–Negative Bacterial Infections," Scand. J. Immunol., 30:219–223 (1989).

Golub, E., and Green, D., "Immunology: A Synthesis," Sinauer Associates, Second Edition, p. 531 (1991).

Golub, E., "The Limits of Medicine: How Science Shapes our Hope for the Cure," Times Books/Random House, pp. 117–120 (1994).

Gram et al., "In vitro Selection and Affinity maturation of Antibodies from a Naive Combinatorial Immunoglobulin Library," Proc. Natl. Acad. Sci. (USA), 89:3576–3580 (1992).

Griffiths et al., "Human Anti–Self Antibodies with High Specificity from Phage Display Libraries," EMBO J., 12:725–734 (1993).

Griffiths et al., "Isolation of High Affinity Human Antibodies Directly from Large Synthetic Repertoires," EMBO J., 13:3245–3260 (1994).

Guilbert et al., "Naturally Occurring Antibodies Against Nine Common Antigens in Human Sera," J. Immunol., 128:2779–2787 (1982).

Hartman and Wright, "Identification of Autoantibodies Specific for the Neutrophil Adhesion Glycoproteins CD11b/CD18 in Patients with Autoimmune Disease [Neutropenia]," Blood, 78:1096–1104 (1991).

Hirohata et al., "Frequency Analysis of Human Peripheral Blood B Cells Producing IgM–Rheumatoid Factor," J. Immunol., 145:1681–1686 (1990).

Hoogenboom et al., "Building Antibodies From Their Genes," Rev. Fr. Transfus. Hemobiol., 36:19–47 (1993).

Huse, "Combinatorial Antibody Expression Libraries in Filamentous Phage," Chapter 5 of *Antibody Engineer,* Borrebaeck (ed.), W.H. Freeman and Co. N.Y. (1992).

Huston et al., "Protein Engineering of Single–Chain Fv Analogs and Fusion Proteins," Methods in Enzymology, 203:46–88 (1991).

Kaushik et al., "Comparative Analysis of Natural Antibody Specificities Among Hybridomas Originating from spleen and Peritoneal Cavity of Adult NZB and BALB/c Mince," Scand. J. Immunol., 27:461–471 (1988).

Klein and Horjsi, "Immunology" [Chapter 20, "Immunological Tolerance"], Blackwell Scientific, Second Edition, p. 527 (1997).

Koga et al., "Mouse–Human Chimeric Monoclonal Antibody to Carcinoembryonic Antigen (CEA): In Vitro and In Vivo Activities," Hybridoma, 9:43–56 (1990).

Landsteiner, K., "The Specificity of the Immune Response," quoted in Golub, E., *Immunology: A Synthesis,* Sinauer Associates, pp. 19–25, [1991 book] (1987).

Logtenberg et al., "Analysis of the Human Tonsil B Cell Repertoire by Somatic Hybridization: Occurrence of Both "Monospecific" and "Multispecific" (auto) Antibody-Secreting Cells," Eur. J. Immunol., 17:855–859 (1987).

Mamula et al., "The Specificity of Human Anti–Cycochrome c Autoantibodies that Arise in Autoimmune Disease," J. Immunol, 144:1835–1840 (1990).

Marks et al., "Molecular Evolution of Proteins on Filamentous Phage," J. Biol. Chem., 267:16007–16010 (1992).

McHeyzer–Williams et al., "Clonal Analysis of Autoantibody–Producing Cell Precursors in the Preimmune B Cell Repertoire," J. Immunol., 141:4118–4123 (1988).

Mullinax et al., "Identification of Human Antibody Fragment Clones Specific For Tetanus Toxoid in a Bacteriophage λ Immunoexpression Library," Proc. Natl. Acad. Sci., USA, 87:8095–8099 (1990).

Nossal, B.V.J., "Cellular Mechanisms of Immune[ologic] Tolerance," Ann. Rev. Immunol., 1:33–62 (1983).

Nossal, G.V.J., "Molecular and Cellular Aspects of Immunologic Tolerance," Eur. J. Biochem., 202:729–737 (1991).

Neumaier et al., "Cloning of the Genes for T84.66, an Antibody That Has a High Specificity and Affinity for Carcinoembryonic Antigen, and Expression of Chimeric Human/Mouse T84.66 Genes in Myeloma and Chinese Hamster Ovary Cells," Cancer Research, 50:2128–2134 (1990).

Perelson, A.S., "Immune Network Theory," Immunol. Rev., 110:5–36 (1989).

Persson et al., "Generation of Diverse High–Affinity Human Monoclonal Antibodies by Repertoire Cloning," Proc. Natl. Acad. Sci., 88:2432–2436 (1991).

Ruf et al., "Various Expressions of a Unique Anti–Human Thyroglobulin Antibody Repertoire in Normal State and Autoimmune Disease," Blood, 78:1096–1104 (1991).

Smith et al., "Phage Display," Chem. Rev., 97:391–410 (1997).

Svenson et al., "IgG Autoantibodies Against Interleukin 1α in Sera of Normal Individuals," Scand. J. Immunol., 29:489–492 (1989).

Ura et al., "Studies on Circulating Antibody Against Carcinoembryonic Antigen (CEA) and CEA–like Antigen in Cancer Patients," Cancer Letters, 25:283–295 (1985).

Waterhouse et al., "Combinatorial Infection and in Vivo Recombination: A Strategy for Making Large Phage Antibody Repertoires," Nucl. Acids Res., 21:2265–2266 (1993).

Wilson and Stanfield, "Antibody–antigen Interactions: New Structures and New Conformational Changes," Curr. Opin. Structural Biol., 4:857–867 (1994).

Winter et al., "Making Antibodies by Phage Display Technology," Annu. Rev. Immunol., 12:433–455 (1994).

* cited by examiner

SEQUENCE LISTING

<160> NUMBER OF SEQ ID NOS: 21

<210> SEQ ID NO 1
<211> LENGTH: 93
<212> TYPE: DNA
<213> ORGANISM: oligonucleotide SYNLIB1
<220> FEATURE:
<221> NAME/KEY: misc_feature
<222> LOCATION: (53)..(54)
<223> OTHER INFORMATION: n= a or c or g or t
<221> NAME/KEY: misc_feature
<222> LOCATION: (56)..(57)
<223> OTHER INFORMATION: n= a or c or g or t
<221> NAME/KEY: misc_feature
<222> LOCATION: (59)..(60)
<223> OTHER INFORMATION: n= a or c or g or t
<221> NAME/KEY: misc_feature
<222> LOCATION: (62)..(63)
<223> OTHER INFORMATION: n= a or c or g or t
<221> NAME/KEY: misc_feature
<222> LOCATION: (65)..(66)
<223> OTHER INFORMATION: n= a or c or g or t

<400> SEQUENCE: 1
gcctccacct ctcgagacgg tgaccagggt accttggccc caatagtcaa amnnmnnmnn    60
mnnmnntctt gcacagtaat acacggccgt gtc                                 93

<210> SEQ ID NO 2
<211> LENGTH: 84
<212> TYPE: DNA
<213> ORGANISM: oligonucleotide SYNLIB2
<220> FEATURE:
<221> NAME/KEY: misc_feature
<222> LOCATION: (44)..(45)
<223> OTHER INFORMATION: n= a or c or g or t
<221> NAME/KEY: misc_feature
<222> LOCATION: (47)..(48)
<223> OTHER INFORMATION: n= a or c or g or t
<221> NAME/KEY: misc_feature
<222> LOCATION: (50)..(51)
<223> OTHER INFORMATION: n= a or c or g or t
<221> NAME/KEY: misc_feature
<222> LOCATION: (53)..(54)
<223> OTHER INFORMATION: n= a or c or g or t
<221> NAME/KEY: misc_feature
<222> LOCATION: (56)..(57)
<223> OTHER INFORMATION: n= a or c or g or t

<400> SEQUENCE: 2
gcctccacct ctcgagacgg tgaccagggt accttggccc camnnmnnmn nmnnmnntct    60
tgcacagtaa tacacggccg tgtc                                           84

<210> SEQ ID NO 3
<211> LENGTH: 60
<212> TYPE: DNA
<213> ORGANISM: oligonucleotide SYNLIB4
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t -continued

```
<400> SEQUENCE: 3
gaccagggta ccttggcccc amnnmnnmnn mnntcttgca cagtaataca cggccgtgtc        60

<210> SEQ ID NO 4
<211> LENGTH: 63
<212> TYPE: DNA
<213> ORGANISM: oligonucleotide SYNLIB5
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t

<400> SEQUENCE: 4
gaccagggta ccttggcccc amnnmnnmnn mnnmnntctt gcacagtaat acacggccgt        60
gtc                                                                     63

<210> SEQ ID NO 5
<211> LENGTH: 66
<212> TYPE: DNA
<213> ORGANISM: oligonucleotide SYNLIB6
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t
<221> NAME/KEY: misc_feature
<222> LOCATION: (38)..(39)
<223> OTHER INFORMATION: n= a or c or g or t

<400> SEQUENCE: 5
gaccagggta ccttggcccc amnnmnnmnn mnnmnmnnnt cttgcacagt aatacacggc        60
cgtgtc                                                                  66

<210> SEQ ID NO 6
<211> LENGTH: 69
<212> TYPE: DNA
<213> ORGANISM: oligonucleotide SYNLIB7
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
```

<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t
<221> NAME/KEY: misc_feature
<222> LOCATION: (38)..(39)
<223> OTHER INFORMATION: n= a or c or g or t
<221> NAME/KEY: misc_feature
<222> LOCATION: (41)..(42)
<223> OTHER INFORMATION: n= a or c or g or t

<400> SEQUENCE: 6
gaccagggta ccttggcccc amnmnmnmn mnnmnmnmnm nntcttgcac agtaatacac    60
ggccgtgtc                                                           69

<210> SEQ ID NO 7
<211> LENGTH: 72
<212> TYPE: DNA
<213> ORGANISM: oligonucleotide SYNLIB8
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t
<221> NAME/KEY: misc_feature
<222> LOCATION: (38)..(39)
<223> OTHER INFORMATION: n= a or c or g or t
<221> NAME/KEY: misc_feature
<222> LOCATION: (41)..(42)
<223> OTHER INFORMATION: n= a or c or g or t
<221> NAME/KEY: misc_feature
<222> LOCATION: (44)..(45)
<223> OTHER INFORMATION: n= a or c or g or t

<400> SEQUENCE: 7
gaccagggta ccttggcccc amnmnmnmn mnmnmnmnm nmnntcttg cacagtaata    60 cacggccgtg tc                                                     72

<210> SEQ ID NO 8
<211> LENGTH: 75
<212> TYPE: DNA
<213> ORGANISM: oligonucleotide SYNLIB9
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t
<221> NAME/KEY: misc_feature
<222> LOCATION: (38)..(39)
<223> OTHER INFORMATION: n= a or c or g or t
<221> NAME/KEY: misc_feature
<222> LOCATION: (41)..(42)
<223> OTHER INFORMATION: n= a or c or g or t
<221> NAME/KEY: misc_feature
<222> LOCATION: (44)..(45)
<223> OTHER INFORMATION: n= a or c or g or t
<221> NAME/KEY: misc_feature
<222> LOCATION: (47)..(48)
<223> OTHER INFORMATION: n= a or c or g or t

<400> SEQUENCE: 8
gaccagggta ccttggcccc amnmnmnmn mnmnmnmnm nnmnmnntc ttgcacagta    60 atacacggcc gtgtc                                                 75

<210> SEQ ID NO 9
<211> LENGTH: 78
<212> TYPE: DNA
<213> ORGANISM: oligonucleotide SYNLIB10
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t
<221> NAME/KEY: misc_feature
<222> LOCATION: (38)..(39)
<223> OTHER INFORMATION: n= a or c or g or t
<221> NAME/KEY: misc_feature
<222> LOCATION: (41)..(42)
<223> OTHER INFORMATION: n= a or c or g or t
<221> NAME/KEY: misc_feature
<222> LOCATION: (44)..(45)
<223> OTHER INFORMATION: n= a or c or g or t
<221> NAME/KEY: misc_feature
<222> LOCATION: (47)..(48)
<223> OTHER INFORMATION: n= a or c or g or t
<221> NAME/KEY: misc_feature
<222> LOCATION: (50)..(51)
<223> OTHER INFORMATION: n= a or c or g or t

<400> SEQUENCE: 9
gaccagggta ccttggcccc amnmnmnmn mnmnmnmnm nnmnmnnmn ntcttgcaca    60 gtaatacacg gccgtgtc                                              78

<210> SEQ ID NO 10
<211> LENGTH: 81
<212> TYPE: DNA
<213> ORGANISM: oligonucleotide SYNLIB11
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)

```
<223> OTHER INFORMATION: n= a or c or g or t
<221> NAME/KEY: misc_feature
<222> LOCATION: (38)..(39)
<223> OTHER INFORMATION: n= a or c or g or t
<221> NAME/KEY: misc_feature
<222> LOCATION: (41)..(42)
<223> OTHER INFORMATION: n= a or c or g or t
<221> NAME/KEY: misc_feature
<222> LOCATION: (44)..(45)
<223> OTHER INFORMATION: n= a or c or g or t
<221> NAME/KEY: misc_feature
<222> LOCATION: (47)..(48)
<223> OTHER INFORMATION: n= a or c or g or t
<221> NAME/KEY: misc_feature
<222> LOCATION: (50)..(51)
<223> OTHER INFORMATION: n= a or c or g or t
<221> NAME/KEY: misc_feature
<222> LOCATION: (53)..(54)
<223> OTHER INFORMATION: n= a or c or g or t

<400> SEQUENCE: 10
gaccagggta ccttggcccc amnnmnmnmn mnnmnmnmnm nnmnmnnmn nmnntcttgc    60 acagtaatac acggccgtgt c                                             81

<210> SEQ ID NO 11
<211> LENGTH: 84
<212> TYPE: DNA
<213> ORGANISM: oligonucleotide SYNLIB12
<220> FEATURE:
<221> NAME/KEY: misc_feature
<222> LOCATION: (23)..(24)
<223> OTHER INFORMATION: n= a or c or g or t
<221> NAME/KEY: misc_feature
<222> LOCATION: (26)..(27)
<223> OTHER INFORMATION: n= a or c or g or t
<221> NAME/KEY: misc_feature
<222> LOCATION: (29)..(30)
<223> OTHER INFORMATION: n= a or c or g or t
<221> NAME/KEY: misc_feature
<222> LOCATION: (32)..(33)
<223> OTHER INFORMATION: n= a or c or g or t
<221> NAME/KEY: misc_feature
<222> LOCATION: (35)..(36)
<223> OTHER INFORMATION: n= a or c or g or t
<221> NAME/KEY: misc_feature
<222> LOCATION: (38)..(39)
<223> OTHER INFORMATION: n= a or c or g or t
<221> NAME/KEY: misc_feature
<222> LOCATION: (41)..(42)
<223> OTHER INFORMATION: n= a or c or g or t
<221> NAME/KEY: misc_feature
<222> LOCATION: (44)..(45)
<223> OTHER INFORMATION: n= a or c or g or t
<221> NAME/KEY: misc_feature
<222> LOCATION: (47)..(48)
<223> OTHER INFORMATION: n= a or c or g or t
<221> NAME/KEY: misc_feature
<222> LOCATION: (50)..(51)
<223> OTHER INFORMATION: n= a or c or g or t
<221> NAME/KEY: misc_feature
<222> LOCATION: (53)..(54)
<223> OTHER INFORMATION: n= a or c or g or t
<221> NAME/KEY: misc_feature
<222> LOCATION: (56)..(57)
<223> OTHER INFORMATION: n= a or c or g or t

<400> SEQUENCE: 11
gaccagggta ccttggcccc amnnmnmnmn mnnmnmnmnm nnmnmnnmn nmnnmnntct     60 tgcacagtaa tacacggccg tgtc                                          84

<210> SEQ ID NO 12
<211> LENGTH: 51
<212> TYPE: DNA
```

<213> ORGANISM: oligonucleotide JHSAL

<400> SEQUENCE: 12
gcctgaaccg cctccaccag tcgacacggt gaccagggta ccttggcccc a    51

<210> SEQ ID NO 13
<211> LENGTH: 18
<212> TYPE: DNA
<213> ORGANISM: oligonucleotide CDRFOR

<400> SEQUENCE: 13
cagggtacct tggcccca    18

<210> SEQ ID NO 14
<211> LENGTH: 18
<212> TYPE: DNA
<213> ORGANISM: oligonucleotide CDRBACK

<400> SEQUENCE: 14
gtgtattact gtgcaaga    18

<210> SEQ ID NO 15
<211> LENGTH: 56
<212> TYPE: DNA
<213> ORGANISM: primer HuVH1aBACKSfi

<400> SEQUENCE: 15
gtcctcgcaa ctgcggccca gccggccatg gcccaggtgc agctggtgca gtctgg    56

<210> SEQ ID NO 16
<211> LENGTH: 56
<212> TYPE: DNA
<213> ORGANISM: primer HuVH2aBACKSfi

<400> SEQUENCE: 16
gtcctcgcaa ctgcggccca gccggccatg gcccaggtca acttaaggga gtctgg    56

<210> SEQ ID NO 17
<211> LENGTH: 56
<212> TYPE: DNA
<213> ORGANISM: primer HuVH3aBACKSfi

<400> SEQUENCE: 17
gtcctcgcaa ctgcggccca gccggccatg gccgaggtgc agctggtgga gtctgg    56

<210> SEQ ID NO 18
<211> LENGTH: 56
<212> TYPE: DNA
<213> ORGANISM: primer HuVH4aBACKSfi

<400> SEQUENCE: 18
gtcctcgcaa ctgcggccca gccggccatg gcccaggtgc agctgcagga gtcggg    56

<210> SEQ ID NO 19
<211> LENGTH: 56
<212> TYPE: DNA
<213> ORGANISM: primer HuVH5aBACKSfi

<400> SEQUENCE: 19
gtcctcgcaa ctgcggccca gccggccatg gcccaggtgc agctgttgca gtctgc    56

<210> SEQ ID NO 20
<211> LENGTH: 56

```
<212> TYPE: DNA
<213> ORGANISM: primer HuVH6aBACKSfi

<400> SEQUENCE: 20
gtcctcgcaa ctgcggccca gccggccatg gcccaggtac agctgcagca gtcagg          56

<210> SEQ ID NO 21
<211> LENGTH: 19
<212> TYPE: DNA
<213> ORGANISM: primer

<400> SEQUENCE: 21
cgatccgcca ccgccagag                                                    19
```

PRODUCTION OF ANTI-SELF ANTIBODIES FROM ANTIBODY SEGMENT REPERTOIRES AND DISPLAYED ON PHAGE

CROSS REFERENCE TO RELATED APPLICATIONS

This is a continuation of U.S. Ser. No. 09/197,221 filed Nov. 20, 1998 which is a continuation of U.S. Ser. No. 08/244,597 filed Oct. 26, 1994, now U.S. Pat. No. 5,885,793 and from which priority is claimed under 35 USC §120 which in turn is the US national phase of PCT/GB92/02240 filed Dec. 2, 1992.

This invention relates to the isolation of antibody molecules directed against self antigens, e.g. human antibodies directed against human self antigens. Phage display technology for selection of antibody molecules was described in WO92/01047, PCT/GB92/00883, PCT/GB92/01755 and GB9206372.6. The applicants have realised that antibodies directed against self antigens can be isolated using phage display technology.

Human antiself antibodies are of particular value for in vivo therapeutic and diagnostic purposes, since they avoid the problems arising from the antigenicity of foreign, e.g. mouse antibodies. The most useful human antibodies for therapy are those directed against cell surface molecules, such as receptors, adhesins and integrins, and those directed against circulating biological effector molecules, such as hormones, growth factors and cytokines. It has been extremely difficult to obtain human antibodies against such self antigens. This invention provides a powerful way of obtaining such antibodies.

It is a demanding task to isolate an antibody fragment with specificity against self antigen. Animals do not normally produce antibodies to self antigens, a phenomenon called tolerance (G. J. Nossal Science 245 147–153, 1989). Autoimmune diseases may result from a breakdown in tolerance. In general, vaccination with a self antigen does not result in production of circulating antibodies. It is therefore difficult to raise antibodies to self antigens, particularly in humans. It is possible to raise antibodies that recognise human antigens in an animal such as a mouse, especially if the human antigen is not too closely related to any equivalent in the animal. If a human antibody is then required it is necessary to 'humanise' the antibody, e.g. by CDR grafting (patent GB2188638B).

Phage antibody technology as described in (WO92/01047) offers the ability to isolate such human antibodies directly. in this application, we demonstrate for the first time that antibodies against self-antigens can be isolated from phage libraries derived from, for example, nonimmunised sources and from libraries prepared by synthetic recombination of V-gene sequences, preferably recombination of VH with, DH and JH, and VL With JL sequences. These antibodies are specific for their antigen. This application shows that single libraries derived in this manner can act as a source of both foreign and self antigens and opens up he prospect of a large, universal library to isolate antibodies to any antigen.

It was disclosed in patent application WO92/01047 that antibody fragments can be displayed on the surface of bacteriophage and that they will bind antigen. Antibody fragments can be directly selected using this characteristic. This ability to isolate antibody fragments (Fab, Fv, ScFv and VH) using their display on the surface of filamentous bacteriophage has opened up the prospect of the isolation of antibody specificities (i.e. antibodies directed against a particular antigen) that were difficult or impossible to isolate previously. In particular WO92/01047 demonstrates that antibody specificities can be isolated from a human who has not been specifically immunised ('unimmunised'), even specificities for antigens such as 2-phenyl-5-oxazolone to which humans will not normally be exposed.

In embodiments of this invention, natural or synthetic antibody repertoires derived from a species of mammal, such as human, mouse, rat, sheep, pig, goat, horse or other, are displayed on the surface of a replicable genetic display package (rgdp) and the binding specificity for self is selected by binding to self antigen. In this process, the V gene repertoires are derived from V genes rearranged in vitro or in vivo and or by mutation of (a) rearranged V gene(s). A key feature of the V gene repertoires is that they are extremely diverse in sequence, usually in excess of $10^6$ different members. Indeed it is possible that a sufficiently large library may provide a source of specificities directed against any self antigen. The V-gene repertoires are cloned into the rgdp (for example a filamentous phage vector) such that antibody repertoires are displayed on the surface of the rgdp. The rgdps encoding rare antibody specificities binding to antiself, may be selected by virtue of binding to the self antigen. The antibody repertoires may be cloned in a single replicon or a dual replicon format as described in WO92/01047 and PCT/GB92/00883.

The V genes may be cloned into the genetic material of the rgdp, and expressed as single domains, for example single heavy chain variable domains, so called single domain ligands or "dAbs" (see WO90/01544), or as associated antibody heavy and light chain variable domains.

The two domains could be displayed as separate polypeptide chains (linked as in Fab fragments through non-covalent association of domains and/or disulphide bonds), or as part of the same chain (single chain Fv fragments where the two domains are contained within the same polypeptide chain).

In WO92/01047 and examples 1 to 8 of this application we have used fusion of antibody fragments to gene 3 protein of filamentous bacteriophage for display and selection of antibody fragments. An alternative approach would be to fuse antibody fragments to gene 8 protein or other surface molecules of filamentous bacteriophage.

Isolation of human antibodies directed against human antigens is a demanding task. There are only a limited number of human antigens against which circulating human, antibodies are naturally found. Antibodies are present directed against non-self antigens of human origin. Antibodies directed against human blood group B have been isolated from a phage display library prepared from subjects of blood group 0 (J. D. Marks et al, J. Mol. Biol. 222 581–597, 1991), which recognise the blood group B antigen as foreign.

This invention is concerned with a general method for the isolation of antibodies directed against self antigens which are specific for the antigen concerned. Many patients show significant concentrations of circulating autoantibodies. It is estimated that 10 to 30% of B lymphocytes in normal, healthy individuals are engaged in making autoantibodies (I. R. Cohen and A. Cooke Immunol. Today 7 363–364, 1986). However, the 'natural autoantibodies' produced do not lend themselves to therapeutic use as they are often IgM, low affinity and polyreactive (P. Casali and A. L. Notkins Ann. Rev. Immunol. 7 515–531, 1989; S. Ayrameas Immunol. Today 12 154–159). An immune response against self can arise in autoimmune disease or after infections and a few monoclonal antibodies directed against self antigens have been isolated from patients with autoimmune disease (K. James & G. T. Bell J. Immunol. Methods 100 5–40, 1987). These autoantibodies are frequently specific, but may bind to only a limited range of epitopes on the antigen (M. Bouanani et al Arthritis Rheum. 34 1585–1593, 1991).

The preparation of V gene libraries derived from the mRNA of plasma cells secreting IgG (or IgM) antibody may thus lead to the isolation of antibody fragments derived from autoantibodies. For instance, anti-self antibodies might be isolated from patients with autoimmune diseases, for example anti-acetylcholine receptor antibodies would be expected to be isolated from antibody repertoires made from the IgG mRNA of myasthenia gravis patients. For example, an antibody fragment specific for human thyroid peroxidase has been isolated from a bacteriophage lambda library from a patient with thyroid autoimmune disease (S. Portolano et al Biochem. Biophys. Res. Commun. 179 372–377, 1991). This however required extensive screening of 200,000 plaques to obtain one clone. In addition, this library was derived from thyroid tissue, a procedure not readily applicable in most instances.

In contrast. the power of selection available using the phage system, demonstrated in WO92/01047 allows the ready isolation of autoantibodies from the IgM mRNA of peripheral blood lymphocytes of a donor without disease. We show in example 2 that antibodies binding to human thyroglobulin (which can be found in the sera of people with or without symptomatic autoimmune disease), can be isolated from phage repertoires prepared from unimmunised humans. One would not expect necessarily to be able to obtain antibodies to human thyroglobulin by immunising a human with human thyroglobulin, notwithstanding the presence of thyroglobulin autoantibodies in many people. Autoantibodies against thyroglobulin in normal sera have been reported often to have a high degree of polyreactivity (S. Ayrameas, 1991 supra). In contrast, those which are isolated using a method according to the present invention involving phage antibody technology, see example 2 for instance, are specific for thyroglobulin.

In this application, we also demonstrate that even antibodies against human tumour necrosis factor-a can be isolated as described in example 1 from the same library as the antibodies directed against thyroglobulin. Many self antigens do not have detectable associated circulating autoantibodies. Further, example 3 shows the isolation of antibodies against the self antigens mucin, carcinoembryonic antigen (CEA) and CD4, antibodies to which have not been reported in normal sera. Moreover, these antibodies are specific, whereas there is often a high degree of polyreactivity in natural autoantibodies which can sometimes be found. The vast majority of self antigens do not have detectable associated circulating autoantibodies. Thus the isolation of antiself antibodies as described in this invention opens the prospect of the direct isolation of human antibodies binding to human antigens for a number of purposes such as antibodies which bind to circulating hormones to block, modify or potentiate their action or antibodies that bind to cell surface antigen for imaging or killing for example of cancer cells.

The origin of the V genes that contribute to anti-self antibodies isolated from phage display libraries is not clear. Tolerance to self antigens by the immune system (preventing the generation of antibodies directed against them) is mediated by either clonal deletion or functional inactivation (anergy) of self-reactive B lymphocytes (D. A. Nemazee & K. Burki, Nature 337 562–566, 1989; C. C. Goodnow et al., Nature 334 676–682, 1988; S. B. Hartley et al., Nature 353 765–769, 1991; D. M. Russell et al., Nature 354 308–311, 1991). In either case little circulating anti-self antibody is detectable for most antigens. However, in the case of anergy, functionally inactivated self-reactive cells from the B cell lineage persist in peripheral lymphoid organs leading to cells in circulation. These rare lymphocytes with anti-self specificity may provide heavy or light chain partners (or even both) for phage antibodies with anti-self specificities. Alternatively, such anti-self specificities may arise from the combination in the library of a VH domain with a VL domain to give a specificity that is normally deleted if it occurs in nature. For this reason, combinatorial libraries and 'chain-shuffled' libraries such as described in patent application WO92/01047 may be a particularly rich source of anti-self antibodies. A selection procedure of great power, such as that provided by phage antibodies, is required to obtain such rare anti-self antibodies.

The degree of somatic mutation observed in antiself antibody fragments isolated by phage technology in this application indicates that some have germ line sequences and have therefore arisen from virgin B cells. Other antibodies isolated by phage antibody technology in this application show somatic hypermutation indicating that the V genes have been stimulated by antigen, either a foreign cross reactive antigen or other foreign antigens. In both cases the antibody fragments isolated using phage technology will usually be a combination of VH and VL domains not originally present in the B lymphocytes and the power of phage technology, as described in this application enables their isolation.

According to the present invention there is provided a method of obtaining a member of a specific binding pair (sbp member), which sbp member has an antigen binding site with binding specificity for an antigen which is a self antigen of a species of mammal, the method comprising:

(a) providing a library of replicable genetic display packages (rgdps), each rgdp displaying at its surface an sbp member, and each rgdp containing nucleic acid with sequence derived from said species of mammal and encoding a polypeptide chain which is a component part of the sbp member displayed at the surface of that rgdp;

(b) selecting, by binding with said self antigen, one or more sbp members with binding specificity for said self antigen.

The polypeptide component part encoded by the nucleic acid in each rgdp may be a VH or VL domain of an antibody, or any part of an antibody which, either alone or in combination with one or more other component parts, forms an antibody fragment which is capable of binding an antigen. Examples of polypeptide chains which may be used as component parts of an sbp member as described above therefore include, in addition to VH and VL domains, $V_L C_L$, $V_H C_H 1$, scFv fragments, Fab fragments and so on.

Each said sbp member displayed at the surface of an rgdp may be an antibody fragment comprising a $V_H$ domain and a $V_L$ domain.

Each antibody fragment may be a scFv fragment, a Fab fragment, a Fv fragment consisting of the $V_L$ and $V_H$ domain of a single arm of an antibody, a single domain binding ligand consisting essentially of or comprising a heavy-chain variable domain (Fd), or any other fragment which has the capability of binding an epitope or antigen.

The step of providing a library of rgdps may comprise:

combining (i) a first polypeptide chain component part of an sbp member fused to a component of a rgdp which thereby displays said first polypeptide chain component part or population thereof at the surface of rgdps on expression in a recombinant host cell organism, or a population of such a first polypeptide chain component part fused to a said component of a rgdp, with (ii) a second polypeptide chain component part of an sbp member or a population of such a second polypeptide chain component part, to form a library of sbp members displayed at the surface of rgdps;

at least one of said first or second polypeptide chain component part or populations thereof being encoded by nucleic acid which is capable of being packaged using said component of an rgdp.

The step of providing a library of rgdp may comprise:

expressing in a recombinant host organism a first polypeptide chain component part of an sbp member or a population of such a first polypeptide chain component part, fused to a component of an rgdp which thereby displays said polypeptide chain component part at the surface of rgdps;

combining said first polypeptide chain component part or population with a second polypeptide chain component part of an sbp member or a population of such a second polypeptide chain component part, to form a library of rgdps each displaying an sbp member at its surface, at least one of said polypeptide chain component parts being expressed from nucleic acid which is capable of being packaged using said component of an rgdp.

Where the sbp member is an Fab fragment the first and second polypeptide chain component part may be a polypeptide consisting of a $V_L$ and a $C_L$ domain, and the second polypeptide chain component part a polypeptide consisting of a $V_H$ and a $C_H1$ domain.

The combining of first and second polypeptide chain component parts or populations thereof may be at the nucleic acid level with expression vectors each having introduced therein a sequence encoding a first component part and a sequence encoding a sequence component part. On the other hand, the combining may be at the polypeptide level with first component parts not being expressed from the same vectors as second component parts. Indeed, one or other of the first and second component parts may be provided as a soluble library. Details of various formats which may be employed are given in WO92/01047 and PCT/GB92/00883.

The step of providing a library may comprise:

combining (i) nucleic acid which encodes a first polypeptide chain component of an sbp member fused to a component of a rgdp or a population of such a first polypeptide chain component part fused to a component of a rgdp, with (ii) nucleic acid encoding a second polypeptide chain component part of an sbp member or a population thereof, to form a library of nucleic acid, nucleic acid of said library being capable of being packaged using said component of an rgdp;

expressing in a recombinant host organism said first polypeptide chain component part fused to a component of a rgdp or population thereof and said second polypeptide chain component part of an sbp member or a population thereof, to produce a library of rgdps each displaying at its surface an sbp member and containing nucleic acid encoding a first and a second polypeptide chain component part of the sbp member displayed at its surface. Readers are urged to consult WO92/01047, in particular, if further details of any method described herein are desired.

In one embodiment of the present invention both first and second polypeptide chain component parts or populations thereof are expressed from nucleic acid capable of being packaged using said component of an rgdp. This might be when the component parts together form a Fab fragment or, more usually, when each said sbp member displayed at the surface of an rgdp is an scFv antibody fragment.

In one embodiment, each said second polypeptide chain component part or population thereof may be expressed from nucleic acid separate from nucleic acid from which said first polypeptide chain component part or population thereof is expressed. The nucleic acid encoding the first polypeptide chain component part may be on the same expression vector as the nucleic acid encoding the second polypeptide chain component part, but separate from it so that, for example, Fab fragments are produced. Alternatively, the nucleic acid encoding the first polypeptide chain component part may be on a different expression vector from the nucleic acid which encodes a second polypeptide chain component part. Where a first and second polypeptide chain component part are both encoded on the same expression vector then they may be expressed as scFv fragments, where a VH domain is joined to a VL domain by a polypeptide linker, so that each scFv is a single polypeptide chain.

Each sbp member displayed at the surface of an rgdp is an Fab antibody fragment.

The nucleic acid may be derived from, e.g. rearranged V genes of, an unimmunised mammal, for example a mouse, rat, rabbit, sheep, pig, horse, goat, dog or human. Preferably the species of mammal is human, since it is most difficult to obtain antibodies which recognise (i.e. bind specifically) human self antigens.

The nucleic acid may be derived from a library prepared by artificial or synthetic recombination of V-gene segments, which may be germ-line V-gene sequences. The library may be totally synthetic.

Sbp members selected in (b) displayed at the surface of rgdps may be selected or screened to provide an individual sbp member or a mixed population of said sbp members associated in their respective rgdps with nucleic acid encoding said sbp member or a polypeptide chain thereof. Rgdp phage displaying sbp members selected in (b) may be grown to increase their numbers before any subsequent further selection or screening. Nucleic acid which encodes a selected or screened sbp member and which is derived from an rgdp which displays at its surface a selected or screened sbp member may be used to express an sbp member or a fragment of derivative thereof in a recombinant host organism.

The present invention encompasses any method wherein nucleic acid from one or more rgdps selected from the library by binding with a self antigen is taken and used to provide encoding nucleic acid in a further method (according to any embodiment of the present invention or not) to obtain an individual sbp member or a mixed population of sbp members, or encoding nucleic acid therefor.

The expression end product, selected sbp member, may be modified to produce a derivative thereof.

The expression end product or derivative thereof may be used to prepare a therapeutic or prophylactic medicament or a diagnostic product.

The present invention also encompasses antibody fragments, derivatives thereof, including whole antibodies and fusions with enzymes, obtained using any method described herein according to the present invention.

According to an aspect of the present invention there is provided use, in any method according to embodiment of the present invention described here a kit comprising a library of vectors each comprise nucleic acid which is capable of being package and which encodes a polypeptide chain component part of an antibody for display at the surface of rgdps.

There is also provided by the present invention use, in any method according to any embodiment of the present invention described herein, of a kit comprising a library of rgdps each containing nucleic acid encoding at least one polypeptide chain component part of an antibody.

The present invention provides generally a method for producing a replicable genetic display package (rgdps) or population of such rgdps, which method comprises he steps of:

(a) inserting a nucleotide sequence encoding a binding molecule which is a member of a specific binding air and an anti-self antibody, within a viral genome;

(b) culturing the virus containing said nucleotide sequence so that said binding molecule is expressed and displayed by the virus at its surface.

The present invention also provides a method for selecting a rgdp specific for a particular self-antigen epitope which comprises producing a population of such rgdps and the additional step of selecting for said binding molecule which is an anti-self antibody by contacting the population with said epitope so that individual rgdps with the desired specificity may bind to said epitope. The method may comprise one or more of the additional steps of: (i) separating any bound rgdps from the epitope; (ii) recovering any separated rgdps and (iii) using he inserted nucleotide sequences from any separated rgdps in a recombinant system to produce the binding molecule separate from the virus. The selection step may isolate the nucleotide sequence encoding the binding molecule of desired specificity, by virtue of said binding molecule being expressed in association with the surface of the virus in which said encoding nucleic acid is contained.

The present invention also provides a method of producing a multimeric member of a specific binding pair (sbp) which is an anti-self antibody, which method comprises:

expressing in a recombinant host organism a first polypeptide chain of said sbp member or a genetically diverse population of said sbp member fused to a component of a secreted replicable genetic display package (rgdp) which thereby displays said polypeptide at the surface of the package, and expressing in a recombinant host organism a second polypeptide chain of said multimer and causing or allowing the polypeptide chains come together to form said multimer as part of said rgdp at least one of said polypeptide chains being expressed from nucleic acid that is capable of being packaged using said component therefor, whereby the genetic material of each said rgdp encodes a said polypeptide chain.

Both said chains may be expressed in the same host organism.

The first and second chains of said multimer may be expressed as separate chains from a single vector containing their respective nucleic acid.

At least one of said polypeptide chains (or polypeptide chain component parts) may be expressed from a phage vector.

At least one of said polypeptide chains may be expressed from a phagemid vector, the method including using a helper phage, or a plasmid expressing complementing phage genes, to help package said phagemid genome, and said component of the rgdp is a capsid protein therefor. The capsid protein may be absent, defective or conditionally defective in the helper phage.

The method may comprise introducing a vector capable of expressing said first polypeptide chain, into a host organism which expresses said second polypeptide chain in free form, or introducing a vector capable of expressing said second polypeptide in free form into a host organism which expresses said first polypeptide chain.

Each of the polypeptide chain may be expressed from nucleic acid which is capable of being packaged as a rgdp using said component fusion product, whereby encoding nucleic acid for both said polypeptide chains are packaged in respective rgdps.

The fusions may be expressed in the absence of the rgdp display component, perhaps capsid, expressed in wild-type form.

The capsid protein may be absent, defective or conditionally defective in the helper phage.

The host cell may be a mutator strain which introduces genetic diversity into the sbp member nucleic acid.

The rgdp may be a bacteriophage, the host a bacterium, and said component of the rgdp a capsid protein for the bacterophage. The phage may be a filamentous phage. The phage may be selected from the class I phases fd, M13, f1, If1, ke, ZJ/Z, Ff and the class II phases Xf, Pf1 and Pf3. The phage may be fd or a derivative of fd. The derivative may be tetracycline resistant. The said sbp member or polypeptide chain thereof may be expressed as a fusion with the gene III capsid protein of phage fd or its counterpart in another filamentous phage. The sbp member or polypeptide chain thereof may be inserted in the N-terminal region of the mature capsid protein downstream of a secretory leader peptide. The sequence may be inserted after amino acid +1 of the mature protein. The site for insertion may be flanked by short sequences corresponding to sequences which occur at each end of the nucleic acid to be inserted.

The host may be *E. coli.*

Nucleic acid encoding an sbp member polypeptide may be linked downstream to a viral capsid protein through a suppressible translational stop codon, so that under conditions where the stop is supressed fusion proteins are produced comprising sbp member polypeptide and viral capsid protein, while under non-supressing conditions free form sbp member polypeptides are produced.

Selection systems and assay formats are discussed elsewhere in this text. In these systems and formats, the gene sequence encoding the binding molecule (eg. the antibody) of desired specificity is separated from a general population of rgdps having a range of specifies, by the fact of its binding to a specific target (eg the antigen or epitope). Thus the rgdps formed by said expression may be selected or screened to provide an individual sbp member or a selected mixed population of said sbp members associated in their respective rgdps with nucleic acid encoding said sbp member or a polypeptide chain thereof. The rgdps may be selected by affinity with a member complementary to said sbp member.

Any rgdps bound to said second member may be recovered by washing with an eluant. The washing conditions may be varied in order to obtain rgdps with different binding affinities for said epitope. Alternatively, to obtain eg high affinity rgdps, the complementary member (eg an epitope) may be presented to the population of rgdps (eg pAbs) already bound to a binding member in which case pAbs with a higher affinity for the epitope will displace the already bound binding member. Thus the eluant may contain a molecule which competes with said rgdp for binding to the complementary sbp member. The rgdp may be applied to said complementary sbp member in the presence of a molecule which competes with said package for binding to said complementary sbp member. Nucleic acid derived from a selected or screened rgdp may be used to express said sbp member or a fragment or derivative thereof in a recombinant host organism. Nucleic acid from one or more rgdps may be taken and used to provide encoding nucleic acid in a further said method to obtain an individual sbp member or a mixed population of sbp members, or encoding nucleic acid therefor. The expression end product may be modified to produce a derivative thereof.

A preferred source for the generation of diverse libraries from unimmunised humans is IgM mRNA. It is was found in example 43 of WO92/01047 that antibody fragments directed against turkey egg lysozyme and 2-phenyl-5-oxazolone were much more readily isolated from a phage library derived from the IgM mRNA from unimmunised human donors, than from one prepared from IgC mRNA. Furthermore, no 2-phenyl-5-oxazolone binding antibody fragments could be isolated from a library of 2000000 phage antibody clones prepared from IgGmRNA of unimmunised mice (T. Clackson et al, Nature 352 624–628. 1991). Examples 1 to 3 of this application shot the isolation of antibodies specific for self antigen from the IgM library. Although in these samples, an antiself specificities have been selected as single chain Fv fragments in a single replicon format, antibody specificities could be selected as Fab fragments in a single replicon format or in a dual combinatorial, dual replicon format (Hoogenboom et al, 1991 supra) for instance using recombination with the 1oxP system (PCT/GB92/,00863).

Phage libraries may be prepared which are enriched for antibodies directed against self. B lymphocytes express surface IgM and surface IgD before stimulation with antigen but express little soluble IgM or IgD.

These unstimulated cells are more likely to contain antibody genes with anti-self specificities. In contrast, terminally differentiated plasma cells which secrete soluble antibodies express little surface immunoglobulin. The preparation of cDNA for phage library preparation using primers which are specific for surface IgM or surface IgD will produce a repertoire of antibody genes enriched for the naive, unselected genes encoding V domains. In B lymphocytes which have been functionally silenced by exposure to self there are greatly reduced levels of surface IgM but unchanged levels of surface IgD (C. C. Goodnow et al. supra). Hence, a primer specific for surface IgD may be particularly suitable for isolation of anti-self antibodies.

However, as demonstrated in this application, IgM mRNA from unselected peripheral blood lymphocytes is one preferred source of V genes for antiself specificities. Other sources of such anti-self antibodies may be fetal mRNA or cord blood mRNA (P. M. Lydyard et al Scand J Immunol 31 33–43, 1990).

There is the potential for making repertoires for phage display using the original combination of VH and VL domains by the use of PCR and linkage of the genes encoding them within cells expressing these domains. The principle of 'In cell PCR', where the original VH/VL pairing is maintained, was demonstrated in PCT/GB92/01483 and described in Embleton et al in Nucleic Acids Res., 20, 3831–3837, 1992. This may be particularly useful if lymphocytes can be selected at a stage before the deletion of clones expressing anti-self antibodies.

In one embodiment of this invention, V gene sequences, or even libraries prepared by the synthetic recombination of V, D and J segments may be used. These act as a rich source of anti-self antibodies. In examples 5 to 7, we demonstrate that anti-self specificities against TNF, human anti-rhesus D antibody (OAK3) and human thyroglobulin can be isolated from a phage antibody library prepared by the synthetic joining of V, D and J segments. The use of germ line V genes for this purpose, as shown in examples 5 to 7, should be valuable for the isolation of anti-self antibodies as there is some evidence that B lymphocytes directed against soluble self antigens are functionally silenced and those directed against multivalent membrane bound self antigen are eliminated (S. B. Hartley et al., supra; D. M. Russell et al., supra). Thus, the use of synthetic libraries made by VH, DH, JH or VK, JK or VL, JL recombination in vitro or its equivalent may be particularly advantageous for isolation of antibodies directed against multivalent membrane bound self antigens.

In examples 5 to 7 we have used synthetic VH CDR3 segments incorporating sequences of random bases at the V-D-J joining region and linked them to germ line VH gene segments. Other strategies may be used such as making each of the CDR loops of random sequence or making the CDR loops of known canonical structures (C. Chothia et al, Nature 342 877–893, 1989) and incorporating random sequence elements. The germ line nature of the V and J segments could be altered by incorporation of specific or random alterations to the sequence or by using somatically mutated V gene regions. The strategy used in examples 5 to 7 has the advantage that the loop structures of the V gene segments form only a limited number of distinct folds and combinations of folds (C. Chothia et al J. Mol. Biol. 227 779–817, 1992) and have presumably evolved for stability and to create a distribution and range of binding sites well suited to match the structure of antigens. Moreover, the framework regions and first two hypervariable loops of both heavy and light chains of the synthetic human antibodies are likely to be identical in many different individuals. Such synthetic human antibodies could be less immunogenic than entirely artificial structures.

A further but less preferred alternative to the above natural and synthetic phage display libraries would be to prepare random mutagenesis libraries displayed on phage, derived from one or a few human antibody molecules and selecting anti-self antigen specificities from these.

SELECTION

Individual rgdps eg pAbs expressing the desired specificity for an antigen, can be isolated from a library using the conventional screening techniques (e.g. as described in Harlow, E., and Lane, D., 1988, supra Gherardi, E et al. 1990. J. Immunol. meth. 126 p61–68).

The applicants have also devised selection techniques that are practicable because of the unique properties of rgdps. The general outline of some screening procedures is illustrated in FIG. 5 using pAbs as an example type of rgdp.

The population/library of pAbs to be screened could be generated from immunised or other animals; or be created in vitro by mutagenising pre-existing phage antibodies (using techniques well-known in the art such as oligonucleotide directed mutagenesis (Sambrook, J., et al., 1989 Molecular Cloning a Laboratory Manual, Cold Spring Harbor Laboratory Press) but are preferably derived from unimmunised humans or artificial recombination of human V segments, as described elsewhere. This population can be screened in one or more of the formats described below with reference to FIG. 5, to derive those individual pAbs whose antigen binding properties are different from sample c.

Binding Elution

FIG. 5(i) shows antigen (ag) bound to a solid surface (s) the solid surface (s) may be provided by a petri dish, chromatography beads, magnetic beads and the like. The population/library of pAbs is then passed over the ag, and those individuals p that bind are retained after washing, and optionally detected with detection system d. A detection system based upon anti-fd antisera may be used (see, for instance, Example 4 of WO92/01047). If samples of bound population p are removed under increasingly stringent conditions, the binding affinity represented in each sample will increase. Conditions of increased stringency can be obtained, for example, by increasing the time of soaking or changing the pH of the soak solution, etc.

Competition

Referring to FIG. 5(ii) antigen ag can be bound to a solid support s and bound to saturation by the original binding molecule c. If a population of mutant pAb (or a set of unrelated pAbs) is offered to the complex, only those that have higher affinity for antigen ag than c will bind. In most examples, only a minority of population c will be displaced by individuals from population p. If c is a traditional antibody molecule, all bound material can be recovered and bound p recovered by infecting suitable bacteria and/or by use of standard techniques such as PCR.

An advantageous application is where ag is used as a receptor and c the corresponding ligand. The recovered bound population p is then related structurally to the receptor binding site/and or ligand. This type of specificity is known to be very useful in the pharmaceutical industry.

Another advantageous application is where ac is an antibody and c its antigen. The recovered bound population p is then an anti-idiotype antibody which have numerous uses in research and the diagnostic and pharmaceutical industries.

At present t is difficult to select directly for anti-idiotype antibodies. pAbs would give the ability to Ad D do this directly by binding pAb libraries (eg a naive library) to B cells (which express antibodies on their surface) and isolating those phage that bound well.

In some instances it may prove advantageous to pre-select population p. For example, in the anti-idiotype example above, p can be absorbed against a related antibody that does not bind the antigen.

However, If c is a pAb, then either or both c and p can advantageously be marked in some way to both distinguish and select for bound p over bound c. This marking can be physical, for example, by pre-labelling p with biotin; or more advantageously, genetic. For example, c can be marked with an EcoB restriction site, whilst p can be marked with an EcoK restriction site (see Carter, P. et al., 1985, Nucl. Acids Res. 13, 4431–4443). When bound p+c are eluted from the antigen and used to infect suitable bacteria, there is restriction (and thus no growth) c population c (i.e. EcoB restricting bacteria in this example). Any phage that grew, would be greatly enriched for those individuals from p with higher binding affinities. Alternatively, the genetic marking can be achieved by marking p with new sequences, which can be used to specifically amplify p from the mixture using PCR.

Since the bound pAbs can be amplified using for example PCR or bacterial infection, it is also possible to rescue the desired specificity even when insufficient individuals are bound to allow detection via conventional techniques.

The preferred method for selection of a phage displaying a protein molecule with a desired specificity or affinity will often be elution from an affinity matrix with a ligand. Thus, self antigen or fragments thereof may be used to elute specific phage antibodies from self antigen bound to a matrix. Alternatively, the homologous antigen from a different species may be bound to a matrix, a phage antibody library bound, and phage antibodies specific for the self antigen may be eluted using self antigen. For instance, a bovine antigen may be bound to the matrix, a human phage antibody library bound and human antigen used for elution. Antiself antibodies thus isolated will be specific for epitopes shared between the bovine and human antigens. A further but less preferred alternative may be to bind the phage non-specifically to a column and elute with self antigen. For instance, if a Fab phage library is bound to an anti-Fab affinity column, it may be washed at a pH which does not elute non-specific phage and then washed with solution which is the same except it contains self antigen, eluting by virtue of the higher affinity for the mobile phase of phage expressing antibodies against the self antigen.

For each of these formats elution with increasing concentrations of ligand should elute phage displaying binding molecules of increasing affinity. However, when eg a pAb binds to its antigen with high affinity or avidity (or another protein to its binding partner) it may not be possible to elute the pAb from an affinity matrix with molecule related to the antigen. Alternatively, there may be no suitable specific eluting molecule that can be prepared in sufficiently high concentration. In these cases it is necessary to use an elution method which is not specific to eg the antigen-antibody complex. Some of the non-specific elution methods generally used reduce phage viability for instance, phage viability is reduced with time at pH12 (Rossomando, E. F. and Zinder N. D. J. Mol.Biol. 36 387–399 1968). There may be interactions between eg antibodies and affinity matrices which cannot be disrupted without completely removing phage infectivity. In these cases a method is required to elute phage which does not rely on disruption of eg the antibody—antigen interaction. A method was therefore devised which allows elution of bound pAbs under mild conditions (reduction of a dithiol group with dithiothreitol) which do not disrupt phage structure (Example 47 of WO92/01047).

The method of mild elution uses binding of the phage antibody population to biotinylated antigen and binding to streptavidin magnetic beads. Following washing to remove non-binding phage, the phage antibody is eluted and used to infect cells to give a selected phage antibody population. A disulphide bond between the biotin and the antigen molecule allows mild elution with dithiothreitol. A particularly advantageous way of performing this selection is to use biotinylated antigen in excess but at or below a concentration equivalent to the desired dissociation constant for the antigen-antibody binding. This method is advantageous for the selection of high affinity antibodies (R. E. Hawkins, S. J. Russell and G. Winter J. Mol. Biol. 226 889–896, 1992). Antibodies may also be selected for slower off rates for antigen selection as described in (R. E. Hawkins et al, 1992 supra). The concentration of biotinylated antigen may gradually be reduced to select higher affinity phage antibodies. As an alternative, the phage antibody may be in excess over biotinylated antigen in order that phage antibodies compete for binding, in an analagous way to the competition of peptide phage to biotinylated antibody described by J. K. Scott & G. P. Smith (Science 249 386–390. 1990).

This elution procedure is just one example of an elution procedure under mild conditions. A particularly advantageous method would be to introduce a nucleotide sequence encoding amino acids constituting a recognition site for cleavage by a highly specific protease between the foreign gene inserted, in this instance a gene for an antibody fragment, and the sequence of the remainder of gene III.

Examples of such highly specific proteases are Factor X and thrombin. After binding of the phage to an affinity matrix and elution to remove non-specific binding phage and weak binding phage, the strongly bound phage would be removed by washing the column with protease under conditions suitable for digestion at the cleavage site. This would cleave the antibody fragment from the phage particle eluting the phage. These phage would be expected to be infective, since the only protease site should be the one specifically introduced. Strongly binding phage could then be recovered by infecting eg. *E. coli* TG1 cells.

An alternative procedure to the above is to take the affinity matrix which has retained the strongly bound pAb and extract the DNA, for example by boiling in SDS solution. Extracted DNA can then be used to directly transform *E. coli* host cells or alternatively the antibody encoding sequences can be amplified, for example using PCR with suitable primers such as those disclosed herein, and then inserted into a vector for expression as a soluble antibody for further study or a pAb for further rounds of selection.

Another preferred method for selection according to affinity would be by binding to an affinity matrix containing low amounts of ligand.

If one wishes to select from a population of phages displaying a protein molecule with a high affinity for its ligand, a preferred strategy is to bind a population of phage to an affinity matrix which contains a low amount of ligand. There is competition between phage, displaying high affinity and low affinity proteins, for binding to the ligand on the matrix. Phage displaying high affinity protein is preferentially bound and low affinity protein is washed away. The high affinity protein is then recovered by elution with the ligand or by other procedures which elute the phage from the affinity matrix (Example 35 of WO92/01047 demonstrates this procedure).

In summary then, for recovery of the packaged DNA from the affinity step, the package can be simply eluted, it can be eluted in the presence of a homologous sbp member which competes with said package for binding to a complementary sbp member; it could be removed by boiling, it could be removed by proteolytic cleavage of the protein; and other methods will be apparent to those skilled in the art eg. destroying the link between the substrate and complementary sbp member to release said packaged DNA and sbp member. At any rate, the objective is to obtain the DNA from the package so that it can be used directly or indirectly, to express the sbp member encoded thereby.

The efficiency of this selection procedure for pAbs and the ability to create very large libraries means that the immunisation techniques developed to increase the proportion of screened cells producing antibodies of interest will not be an absolute requirement. The technique allows the rapid isolation of binding specificities eg antigen-binding specificities, including those that would be difficult or even unobtainable by conventional techniques, for example, catalytic or anti-idiotypic antibodies. Removal of the animal altogether is now possible, once a complete library of the immune repertoire has been constructed.

Applications of Antibodies to Self Antigens

Human antibodies to cell surface components. The isolation of such antibody specificities would be particularly useful for preparing agents which mediate cell killing for instance of cancer cells, for example using the natural effector function of antibodies. Anti-self antibodies may also be valuable in the preparation of diagnostic in vivo imaging reagents, for instance using radioisotopes.

Antibodies directed against cell surface components of specific T-cell subsets could be used therapeutically (D. Wraith et al Cell 57 709–715, 1989; L. Steinman and R. Mantegazza FASEB J. 4 2726–2731, 1990), for instance to prevent T cell action causing rheumatoid arthritis.

Human Antibodies Modifying the Function of Self Molecules

Antibodies can be isolated which modify the action of self molecules such as hormones, growth factors and receptors through their binding to a specific epitope on the molecule. Multifunctional proteins may have both desirable and undesirable characteristics, particularly if they are used therapeutically. For instance, the lymphokine TNF (tumour necrosis factor) binds to, at least two different classes of cell receptors- one commonly found on vascular endothelial cells, the other commonly found on tumour cells. A mouse antibody to TNF has been made which prevents TNF from binding to endothelial cell receptors while still allowing it to bind to tumour cells thus allowing attack on the tumours without toxic side effects mediated through endothelial cells (Patent application PCT/AU90/00337). For therapeutic use of antibody modifiers of hormone or growth factor molecules, it would be preferable to have a human antibody specificity isolated directly through selection from a phage library.

Human Anti-idiotypes

Anti-idiotype antibodies (antibodies directed against the antigen combining sites formed by the variable domains of human antibodies) are conventionally made by isolating an antibody against an antigen and then using this isolated antibody as an immunogen to raise antibodies directed against it. If the original antibody is directed against a hormone or growth factor, the relationship between antigen and antibody combining sites means that the anti-idiotype may mimic in some aspects the hormone or growth factor and bind to the receptor for these molecules. However, the fraction of anti-idiotype antibodies able to mimic the binding of the hormone to the receptor would be expected to be small. Furthermore, the deletion of antiself lymphocytes would mean that using the conventional route to anti-idiotypes would be difficult for the isolation of human anti-idiotype antibodies mimicking molecules binding human receptors. In this application we show that antibodies directed against the antigen combining sites formed by the variable domains of human antibodies may be directly isolated from phase antibody display libraries, as shown in examples 1 and 4, and it should also be possible to identify the anti-idiotypic antibodies mimicking the binding of the hormone directly by screening for binding to the receptor.

Anti-idiotypes may also be useful for the treatment of autoimmune disease. They could be used to bind to circulating autoantibodies. However, it may be preferable to attack directly antibody producing cells, for instance using a bispecific antibody directed against a cell surface marker as well as an anti-idiotype specificity. Alternatively, plasmaphoresis could be used to remove circulating antibody and the cells treated directly.

Human Antibodies Against Receptors

Human antibodies that bind to receptors, blocking or antagonising ligand function could be selected directly from a phage library displaying antibodies derived from an unimmunised donor.

Human Antibodies to Prevent Transplant Rejection

Antibodies directed against the major histocompatibility complex proteins could be used to treat patients following transplants, or organs prior to transplantation, in order to prevent rejection. Antibodies directed against several lymphocyte cell surface markers have been used for the prevention of rejection in transplants e.g. CD45, CD3, CD4, CD8 and interleukin-2 receptor. Example 3 shows that human antibodies against CD4 can be directly isolated from phage display libraries.

Human Antibodies Against Cytokines

Human antibodies against cytokines would be valuable for treatment of human disease, for example of septic shock with anti-TNF and anti-interleukin 1 antibodies. Examples 1 and 6 show that human antibodies against TNF can be isolated directly from phage antibody libraries derived from unimmunised humans or the synthetic recombination of V, D and J fragments. In many cases these cytokine molecules are strongly conserved between species, for instance transforming growth factor-β (TGF-β), and it has proved difficult to isolate antibodies directed against the human molecule even in mice. The isolation of human anti-self antibodies as described in this invention provides a method of obtaining human antibodies with such a specificity.

Human Antibodies for Diagnosis and Treatment of Cardiac Disorders

Human antibodies against clot components e.g. fibrin, would be useful for imaging clots when labelled with radioactivity or for dissolving clots, if for example linked to a clot dissolving enzyme such as urokinase.

Antibodies Triggering Receptor Function

Antibodies may be selected that bind to a cell receptor and trigger a biological response in the cell. This is described in more detail below and in Example 8 describes the isolation of such antibodies.

By cycles of growth and selection, those rgdps binding to the cell receptors are isolated. Some of these rgdps encode binding specificities with the potential (alone or in combination with other binding specificities) to trigger the receptors. These binding specificities are tested alone, or in combination, for triggering the cell receptors.

There are a variety of cell receptors in which the binding of a ligand, for example hormone, growth factor, or peptide triggers a biological event, for example the activation of tyrosine kinase activity, or the opening of an ion channel. The rdgps could be selected for bending to cell receptor (or a related receptor with conserved portions of surface such as from another species), for example by using cells displaying the cell receptor, or using soluble receptor, mobilised on solid phase, or using domains or peptide epitopes of the receptor. Ideally the receptor would be provided in a crosslinked form (as required for its triggering).

Triggering of receptors at the cell surface often seems to involve the relative movement of proteins or subunits. For example, in the neurotransmitter-gated receptors, the five subunits that are arranged symmetrically in the membrane place, delineate an ion pathway down the centre. Binding of the neurotransmitter is thought to alter the size of the central ion channel by causing small rearrangements between the subunits in an allosteric transition. For tyrosine kinase receptors, the ligand appears to drive receptor oligomerisation. Thus antibodies with binding specificities directed against a receptor may have the potential to promote an allosteric change or to promote oligomerisation. The oligomerisation of the receptors may also be promoted by using bivalent or bispecific antibodies.

The soluble antibodies or antibody fragments may be monovalent fragments, for example, single chain Fv fragments or Fab fragments, or bivalent fragments, for example, $Fab_2$ or complete antibody fragments. The bivalency could also be promoted in other ways, for example (1) by encoding a tag, such as a peptide or protein (for example, the subunit of a dimeric protein) that self associates, at the N or C-terminus of the monomeric fragment, (2) using a bivalent antibody that binds to the monovalent fragment, for example, to a common C-terminal tag, or to an antibody constant domain (3) chemical cross-linking.

Bispecific antibody or bispecific fragments could also be made as for the bivalent fragments. (For expression of the bispecific antibody or fragment in the same cell, the genes encoding both specificities would need to be introduced together). The different antibody "arms" could be directed against the same receptor, for example to different epitopes, or to two different receptors (to trigger hybrid receptors).

The direct isolation so anti-self antibodies from phage libraries as described in this invention is important to allow a large number of antibodies to be surveyed for these triggering receptors.

It is appropriate to distinguish the making of antibodies to trigger receptors as is described here and provided as an aspect of the present invention from the "anti-idiotypic route" in which specific antibodies raised in an animal, including man, by vaccinating the said animal with a specific antigen are themselves used to vaccinate another animal, new antibodies termed anti-idiotypic antibodies (Anti-Ids) being produced able to recognise and bind to the first set of antibodies. Some species of these Anti-Ids are able to mimic the specific biological properties of the original antigen. If for example, the antigen were a peptide hormone or a cell receptor, the Anti-Id to the hormone or cell receptor antigen is able to elicit a response of the cell (See Gaulton, G. N. and Greane, M. I., 1986. Idiotypic mimicry of biological receptors. Ann. Rev. Immunol. 4,253–280; Sege, K. and Peterson, P. A., 1978. Use of anti-idiotypic antibodies as cell surface receptor probes. Proc. Natl. Acad. Sci. Usa. 75, 2443–2447 for examples).

The essence of current teaching of Anti-Ids as mimics of antigens is that they are produced as a result of constructing antibodies to antibodies of the original antigen. There is however, some controversy over whether such anti-idiotypes accurately mimic the original antigen (S. J. Davis et al Nature 358 76–79, 1992).

There is therefore a clear distinction between antibodies prepared by an anti-idiotypic route that mimic antigens such as growth factors or hormones, and antibodies that are made directly to the receptors to trigger the receptors. The antibodies derived by an anti-idiotypic route require the antigen (hormone, growth is factor) and will bind to the same epitope on the receptor as the hormone, while the antibodies derived by binding to the receptors need not bind to the same epitope to trigger the receptor. Indeed such antibodies need not mimic a known hormone or growth factor, as their specificity, or binding to receptor (characterised as epitope, on-rate or off-rate) or blood clearance is likely to differ. The process for making the antibodies is also quite different. Anti-idiotypic antibodies are made classically by immunisation of animals, although they can be isolated directly from phage display libraries as described above. Antibodies directed against self receptors are made by selection from V-gene libraries (as described above).

As well as the advantages over the anti-idiotypic route, the antibodies derived directly by receptor binding may even have advantages over the natural hormone or growth factor. Thus receptors that are defective for binding of the natural hormone or growth factor (for example in a genetic disease), may be triggered by an antibody binding at a different epitope.

As therapeutic agents the various isotypes of antibodies or fragments of antibodies carrying the variable regions responsible for the specificity of the molecule have a number of properties having advantages over the bioactive moiety they mimic. For example, unlike the natural hormones their half-life in circulation can be modified readily. Depending on the antibody isotype or fragment chosen, they have half-lives in circulation in a patient ranging from minutes to several weeks. If long term usage or short term clearance is required this can easily be accommodated by choosing the appropriate antibody isotype without need to use slow release devices as implants, or continuous intravenous infusion, etc.

Furthermore, many hormones or tissue growth factors or antigens in general are functionally complex with different epitopes of each of the molecules having various specific functions. Clones of antibody mimics are monofunctional in this respect so could be used to produce one specific biological effect of a hormone without a second effect which latter effect may be disadvantageous to the patient. Thus the lymphokine TNF (tumour necrosis factor) binds to two different classes of cell receptors—one common on vascular endothelial cells, the other common on tumour cells. If the TNF is modified so that it cannot bind to the endothelial cell receptors but can still bind to tumour cell receptors, the tumours are attacked without at the same time inducing the very toxic side effects mediated through the vascular receptors. (This is described in Australian Patent Application PCT/AU90/00337). An antibody mimic able to recognise the tumour cell receptor would be expected to be very specific and kill tumour cells without inducing toxic side effects mediated through the vascular endothelium since it would have no resemblance to the TNF epitope which binds to receptors on the latter.

TERMINOLOGY

Much of the terminology discussed in this section has been mentioned in the text where appropriate.

Self

A self antigen is an antigen or epitope which is capable of binding to an antigen binding site formed by antibody variable domain(s) and which is conserved between members of a species of animal and native to the body.

The immune system tries to avoid making antibodies to self antigens. It has been suggested that (i) sequences of germ line V gene segments have been evolved under pressure to be directed towards foreign, e.g. pathogen, antigens and epitopes, and away from being able to provide antibodies which will bind self antigens, and (ii) that, in addition to this, immune tolerance causes those combinations of gene segments encoding anti-self antibody which do arise, to be deleted or anergised. Consequently, there are not normally circulating antibodies against these antigens except in disease states, eg autoimmune diseases. A self antigen may be one which does not vary between individuals of a species. A self antigen may be one for which there is normal allelic variation throughout a population. Immunisation of one individual in a species with a self antigen would not normally be expected to result in generation, or detection, of antibodies to the antigen, except perhaps when tolerance is deliberately broken. Antibodies to a self-antigen may only be present in an individual who is suffering from autoimmune disease. On the other hand, there are some self antigens to which circulating antibodies can be found in a sub-population of normal individuals of a species.

A self antigen may be an antigen recognised by B-cell surface antibodies but not by antibodies which can be found circulating. It might not be possible to detect or obtain circulating antibodies to a self antigen except perhaps when the individual is suffering from an autoimmune disease or syndrome.

An anti-self antibody or antibody fragment is an antibody or fragment thereof which has binding specificity for a self antigen. It may recognise an epitope which is found only on a self antigen, or it may be cross-reactive with an antigen which individuals of the species will recognise as foreign. The present invention is particularly well suited to the production and isolation of antibody fragments which bind only a self antigen.

Specific Binding Pair

This describes a pair of molecules (each being a member of a specific binding pair) which are naturally derived or synthetically produced. One of the pair of molecules, has an area on its surface, or a cavity which specifically binds to, and is therefore defined as complementary with a particular spatial and polar organisation of the other molecule, so that the pair have the property of binding specifically to each other. Examples of types of specific binding pairs are antigen-antibody, biotin-avidin, hormone-hormone receptor, receptor-ligand, enzyme-substrate, lgG-protein A.

Multimeric Member

This describes a first polypeptide which will associate with at least a second polypeptide, when the polypeptides are expressed in free form and/or expressed on the surface of a substrate. The substrate may be provided by a bacteriophage. Where there are two associated polypeptides, the associated polypeptide complex is a dimer, where there are three, a trimer etc. The dimer, trimer, multimer etc or the multimeric member may comprise a member of a specific binding pair.

Example multimeric members are heavy domains based on an immunoglobulin molecule, light domains based on an immunoglobulin molecule, T-cell receptor subunits.

Replicable Genetic Display Package (Radp)

This describes a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair eg. heavy or light chain domains based on an immunoglobulin molecule, an enzyme or a receptor etc.

The particle may be a virus eg. a bacteriophage such as fd or M13.

Package

This describes a replicable genetic display package in which the particle is displaying a member of a specific binding pair at its surface. The package may be a bacteriophage which displays an antigen binding domain at its surface. This type of package has been called a phage antibody (pAb).

Antibody

This describes an immunoglobulin whether natural or partly or wholly synthetically produced. The term also covers any protein having a binding domain which is, or is homologous to, an immunoglobulin binding domain. These proteins can be derived from natural sources, or partly or wholly synthetically produced.

Example antibodies are the immunoglobulin isotypes and the Fab, F(ab$^1$)$_2$, scFv, Fv, dAb, Fd fragments.

Immunoglobulin Superfamily

This describes a family of polypeptides, the members of which have at least one domain with a structure related to that of the variable or constant domain of immunoglobulin molecules. The domain contains two β-sheets and usually a conserved disulphide bond (see A. F. Williams and A. N. Barclay 1988 Ann. Rev Immunol. 6, 381–405).

Example members of an immunoglobulin superfamily are CD4, platelet derived growth factor receptor (PDGFR), intercellular adhesion molecule (ICAM). Except where the context otherwise dictates, reference to immunoglobulins and immunoglobulin homologs in this application includes members of the immunoglobulin superfamily and homologs thereof.

Homologs

This term indicates polypeptides having the same or conserved residues at a corresponding position in their primary, secondary or tertiary structure. The term also extends to two or more nucleotide sequences encoding the homologous polypeptides.

Example homologous peptides are the immunoglobulin isotypes and the TIM barrel enzymes.

Functional

In relation to a sbp member displayed on the surface of a rgdp, means that the sbp member is presented in a folded form in which its specific binding domain for its complementary sbp member is the same or closely analogous to its native configuration, whereby it exhibits similar specificity with respect to the complementary sbp member.

Genetically Diverse Population

In connection with sbp members or polypeptide components thereof, this is referring not only to diversity that can exist in the natural population of cells or organisms, but also diversity that can be created by artificial mutation in vitro or in vivo.

Mutation in vitro may for example, involve random mutagenesis using oligonucleotides having random mutations of the sequence desired to be varied. In vivo mutagenesis may for example, use mutator strains of host microorganisms to harbour the DNA (see Example 38 of WO 92/01047). The words "unique population" may be used to denote a plurality of, e.g., polypeptide chains which are not genetically diverse, i.e., they are all the same. A restricted population is one which is diverse but less so than the full repertoire of an animal or a library, synthetic or otherwise. The diversity may have been reduced by prior selection, e.g., using antigen binding specificity.

Domain

A domain is a part of a protein that is folded within itself and independently of other parts of the same protein and independently of a complementary binding member. A folded unit is a specific combination of a α-helix and/or β-sheet structure. Domains and folded units contain structures that bring together amino acids that are not adjacent in the primary structure.

Free Form

This describes the state of a polypeptide which is not displayed by a replicable genetic display package.

Conditionally Defective

This describes a gene which expresses a defective polypeptide under one set of conditions, but expresses a different but related non-defective polypeptide under another set of conditions. An example, is a gene containing an amber mutation expressed in non-suppressing or suppressing hosts respectively.

Alternatively, a gene may express a protein which is defective under one set of conditions, but not under another set. An example is a gene with a temperature sensitive mutation.

Suppressible Translational Stop Codon

This describes a codon which allows the translation of nucleotide sequences downstream of the codon under one set of conditions, but under another set of conditions translation ends at the codon. Example of suppressible translational stop codons are the amber, ochre and opal codons.

Mutator Strain

This is a host cell which has a genetic defect which causes DNA replicated within it to be mutated with respect to its parent DNA. Example mutator strains are NR9046mutD5 and NR9046 mut T1 (see Example 38 of WO92/01047).

Helper Phage

This is a phage which is used to infect cells containing a defective phage genome and which functions to complement the defect. The defective phage genome can be a phagemid or a phage with some function encoding gene sequences removed. Examples of helper phages are M13KO7, M13KO7 gene III no. 3; and phage displaying or encoding a binding molecule fused to a capsid protein.

Vector

This is a DNA molecule, capable of replication in a host organism, into which a gene is inserted to construct a recombinant DNA molecule.

Phage Vector

This is a vector derived by modification of a phage genome, containing an origin of replication for a bacteriophage, but not one for a plasmid.

Phagemid Vector

This is a vector derived by modification of a plasmid genome, containing an origin of replication for a bacteriophage as well as the plasmid origin of replication.

Secreted

This describes a rgdp or molecule that associates with the member of a sbp displayed on the rgdp, in which the sbp member and/or the molecule, have been folded and the package assembled externally to the cellular cytosol.

Repertoire of Rearranged Immunoglobulin Genes

A collection of naturally occurring nucleotides eg DNA sequences which encoded expressed immunoglobulin genes in an animal. The sequences are generated by the in vivo rearrangement of eg V, D and J segments for H chains and eg the V and J segments for L chains. Alternatively the sequences may be generated from a cell line immunised in vitro and in which the rearrangement in response to immunisation occurs intracellularly.

Library

A collection of nucleotides eg DNA sequences within clones; or a genetically diverse collection of polypeptides, or specific binding pair members, or polypeptides or sbp members which are displayed on rgdps capable of being selected or screened to provide an individual polypeptide or sbp member or a mixed population of polypeptides or sbp members.

Repertoire of Artificially Rearranged Immunoglobulin Genes

A collection of nucleotides eg DNA sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and segments.

Part or all of the DNA sequences may be derived by oligonucleotides synthesis.

Secretory Leader Peptide

This is a sequence of amino acids joined to the N-terminal end of a polypeptide and which directs movement of the polypeptide out of the cytosol.

Eluant

This is a solution used to breakdown the linkage between two molecules. The linkage can be a non-covalent or covalent bond(s). The two molecules can be members of a sbp.

Derivative

This is a polypeptide which derived from another polypeptide which is encoded by the DNA within a selected rdgp. The derivative polypeptide may differ from the encoded polypeptide by the addition, deletion, substitution or insertion of amino acids, or by the linkage of other molecules to the encoded polypeptide. These changes may be made at the nucleotide or protein level. For example the encoded polypeptide may be a Fab fragment which is then linked to an Fc tail from another source. Alternatively markers such as enzymes, fluoresceins etc may be linked to e.g. Fab, scFv fragments.

Figure 1A:
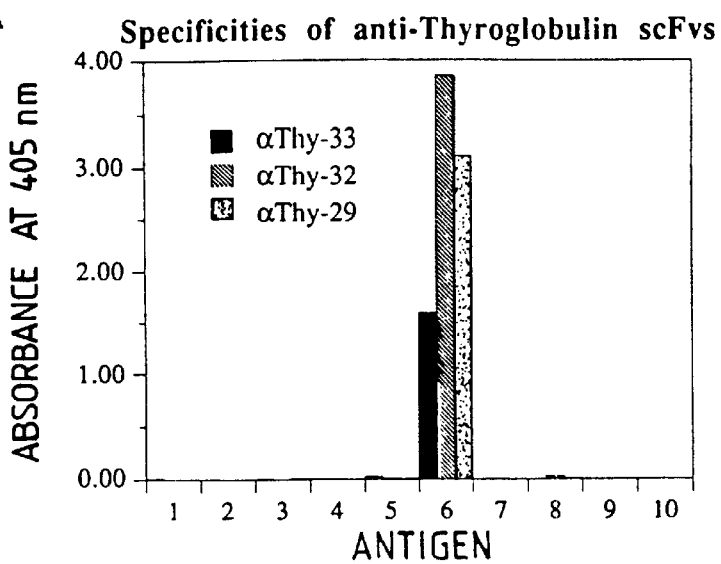
FIGS. 1A–1C show an analysis by ELISA of the specificities of soluble single-chain Fvs (scFvs) isolated from the unimmunised library by selection on bovine thyroglobulin (A), human TNFα (B), or the human mAb Fog-1 (gamma-1, kappa) (C). Binding was determined by ELISA to a panel of proteins, as follows: 1—plastic; 2—hen egg trypsin inhibitor; 3—chymotrypsinogen A; 4—hen egg ovalbumin; 5—keyhole limpet haemocyanin; 6—bovine thyroglobulin; 7—human TNFα; 8—turkey egg-white lysozyme; 9—horse heart cytochrome c; 10—bovine serum albumin; 11—mAb Fog-1.

The present invention is illustrated by the following examples. Oligonucleotide primers and probes mentioned in the text are listed in Table IV. Tables I to IV are found after Example 8.

Example 1 shows the isolation of antibodies directed against human tumour necrosis factor-α and a human monoclonal antibody from a phage library of single chain Fv fragments derived from an unimmunized human.

Example 2 shows the isolation of antibodies binding to human thyroglobulin from a phage library of single chain Fv fragments derived from an unimmunized human.

Example 3 shows the isolation of antibody fragments directed against the self antigens MUC1 mucin, carcinoembryonic antigen (CEA) and recombinant soluble CD4 (rsCD4) from a phage display library of single chain Fv fragments derived from an unimmunized human.

Example 4 shows the further characterization of selected anti-self antibody fragments by DNA sequencing and affinity determinations.

Example 5 shows the creation of a synthetic human library using germ line VH segments.

Example 6 shows the isolation of an antibody fragment binding to human tumour necrosis factor-α from a human germ line synthetic library.

Example 7 shows the creation of a synthetic human library using human germ line VH segments containing VH CDR3 sequences of different lengths and isolation of single chain Fv fragments binding to human thyroglobulin and a human monoclonal antibody.

Example 8 shows the isolation of human antibodies directed against human interleukin-1 receptor molecules which trigger receptor function.

EXAMPLE 1

Isolation of Antibody Fragments Directed Against Self Antigens from a Library of scFvs Made from Unimmunized Blood Donors Naturally occuring V-genes isolated from human PBLs can be constructed into a large library of antibody fragments which contain reactivities against antigens to which the donor has not been exposed (WO92/01047 example 42). We have realised that these libraries may also contain reactivities against self antigens, arising either from self-reactive B-cells which have not been deleted or as non-naturally occuring fragments resulting from VH and VL chain recombination. To test this, we panned a large human scFv library displayed on the surface of a phagemid against human TNF-a and a human IgG/k immunoglobulin.

Methods

Rescue of the Library:

The library of scFvs was constructed from the RNA of human PBLs and has been previously described (WO92/01047 example 42). To rescue phage displaying antibody fragments, approximately $10^9$ E. coli harbouring the phagemid were used to inoculate 50 ml of 2×TY containing 1% glucose and 100 mg/ml of ampicillin (2×TY-AMP-GLU) and grown to an O.D. of 0.8 with shaking. Five ml of this culture was used to innoculate 50 ml of 2×TY-AMP-GLU, $2 \times 10^8$ TU of delta gene 3 helper (M13 D gene III see WO92/01047) were added and the culture incubated at 37° C. for 45 minutes without shaking and then at 37° C. for 45 minutes with shaking. The culture was centrifuged at 4000 r.p.m. for 10 min. and the pellet resuspended in 2 litres of 2×TY containing 100 mg/ml ampicillin and 50 mg/ml kanamycin and grown overnight. Phage were prepared as previously described (WO92/01047 example 42). M13 D gene III was prepared as follows:

35 M13 D gene III helper phage does not encode gene III protein, hence the phage(mid) displaying antibody fragments have a greater avidity of binding to antigen. Infectious M13 D gene III particles are made by growing the helper phage in cells harbouring a pUC19 derivative supplying the wild type gIII protein during phage morphogenesis. The culture was incubated for 1 hour at 37° C. without shaking and then for a further hour at 37° C. with shaking. Cells were spun down (IEC-Centra 8, 4000 revs/min for 10 min), resuspended in 300 ml 2×TY broth containing 100 mg ampicillin/ml and 25 mg kanamycin/ml (2×TY-AMP-KAN) and grown overnight, shaking at 37° C. Phage particles were purified and concentrated from the culture medium by two PEG-precipitations (Sambrook et al., 1990), resuspended in 2 ml PBS and passed through a 0.45 mm filter (Minisart NML; Sartorius) to give a final concentration of approximately $10^{13}$ transducing units/ml (ampicillin-resistant clones).

Panning of the Library:

IMMUNOTUBES (Nunc Fisher Scientific, Leicestershire, UK) were coated overnight in PBS with 4 ml of either 100 mg/ml or 10 mg/ml of recombinant human TNF-α in PBS or 4 ml of 10 mg/ml of Fog-1, a human IgG/k immunoglobulin which recognizes the human red blood cell Rh (D) antigen. Tubes were blocked with 2% Marvel-PBS for 2 hours at 37° C. and then washed 3 times in PBS. Approximately 1013 TU of phage was applied to the tube and incubated for 30 minutes at room temperature tumbling on an over and under turntable and then left to stand for another 1.5 hours. Tubes were washed 10 times with PBS 0.1% TWEEN-20 (neutral detergent) and 10 times with PBS. Phage were eluted by adding 1 ml of 100 mM triethylamine and rotating 15 minutes on an under and over turntable after which the solution was immediately neutralized with 0.5 ml of 1,0 M Tris-HCl, pH 7.4. Phage were then used to infect 10 ml of mid-log E. coli TG1 by incubating eluted phage with bacteria for 30 minutes at 37° C. The E. coli were then plated on TYE plates containing 1% glucose and 100 mg/ml ampicillin. The resulting bacterial library was then rescued with delta gene 3 helper phage as described above to prepare phage for a subsequent round of selection. This process was then repeated for a total of 4 rounds of affinity purification with tube-washing increased to 20 times with PBS, 0.1% TWEEN-20 (neutral detergent) and 20 times with PBS for rounds 3 and 4.

Characterization of Binders:

Eluted phage from the 3rd and 4th rounds of selection were used to infect E. coli HB 2151 and soluble scFv was produced (Marks, et al., 1991) from single colonies for assay. In the case of TNF, phage was also rescued from single colonies. ELISAs were performed as previously described with microtitre plates coated with either 10 µg/ml human TNF-a in 50 mM bicarbonate pH 9.6 or 10 µg/ml Fog-1 in PBS. Clones positive in ELISA were further characterized by PCR fingerprinting (WO92/01047 example 20) and then by sequencing.

Results

Figure 1B:
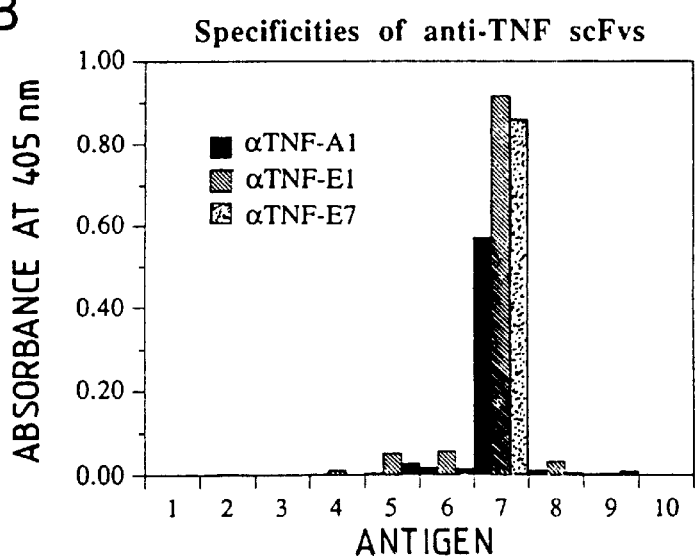
Figure 1C:
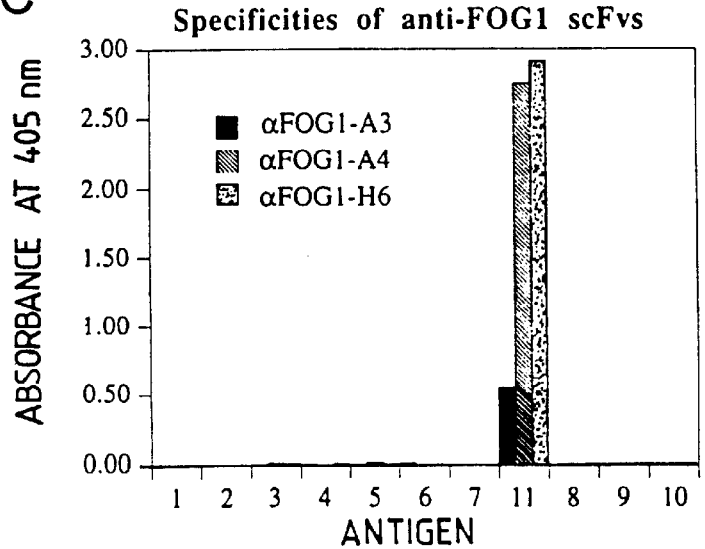

TNF: Soluble scFv from 1536 colonies and phage from 1152 colonies were screened by ELISA. The results are shown in FIG. 1, the key for which is given in the brief description of the figures (supra). Positive clones for binding to TNF-a were further characterized by PCR fingerprinting and sequencing. In this manner, different binders were identified. Four of these have been sequenced.

Fog-1: Soluble scFv from 96 clones was screened by ELISA and positive clones were further characterized by PCR fingerprinting and sequencing. In this manner, four different binders were identifed and sequenced.

EXAMPLE 2

Isolation of Antibody Fragments Specificities Directed Against Human Thyroglobulin from a Library of scFv Fragments using Display on Bacteriophage fd Example 44 of WO92/01047 describes the selection of antibody scFv fragments directed against bovine thyroglobulin from a library of scFv fragments. These were derived from unimmunised humans, expressed on the surface of phage fd, isolated by panning against bovine thyroglobulin. The results demonstrated that it is possible to isolate from a library derived from an unimmunised individual antibody fragments which will bind an antigen to which that individual has never been exposed.

Sixteen clones found by this panning to be specific for bovine thyroglobulin have now been analysed for binding to human thyroglobulin in an ELISA assay (as described in example 44 of WO92/01047). Nine of these clones also bound strongly to human thyroglobulin with is absorbance signals of between 1.0 and 1.6 12 minutes after addition of substrate. No cross-reactivity (signal less than 0.05 after 90 min) was found with a panel of unrelated antigens- hen egg lysozyme, BSA, ovalbumin, chymotrypsinogen, cytochrome c, keyhole limpet hemocyanin, insulin, cardiolipin and DNA.

Thus, antibodies with specificity for epitopes on the human self antigen thyroglobulin can be isolated from libraries prepared from unimmunised humans.

Two clones binding to both human and bovine thyroglobulin, α-Thy23 and α-Thy29, and two clones binding to bovine thyrogobulin only, α-Thy32 and α-Thy33, were sequenced.

EXAMPLE 3

Isolation of Antibody Fragments Directed Against the Human Self-antigens MUC1 Mucin, Carcinoembryonic Antigen (CEA) and Recombinant Soluble CD4 (rsCD4) from a Phage Display Library of Human Single Chain Fv Fragments The phage display library of single chain Fv fragments derived from unimmunized human donors used in Example 1 was used in selection to isolate antibody fragments directed against the self antigens MUC1 mucin, carcinoembryonic antigen (CEA) and recombinant soluble CD4 (rsCD4).

Rescue of the Library

The library was rescued as in example 1 except that the standard helper phage M13K07 (5×10$^{10}$ pfu) was used to rescue the library rather than delta gene 3 helper phage (M13 D gene III).

Selection of Phage Specific for MUC1 Mucin and Carcinoembryonic Antigen (CEA)

The phage were panned for binding using IMMUNO-TUBES (Nunc; Maxisorp, Fisher Scientific, Leicestershire, UK) coated with antigen essentially as (Marks et al., 1991), or were selected on a column of antigen (J. McCafferty et al., Nature 348, 552–554, 1990). The following antigens were used: human recombinant soluble CD4 (rsCD4) (expressed in baculovirus by American Biotechnologies Inc. and supplied by the MRC AIDS Reagent Project [ADP608]; human carcinoembryonic antigen (CEA); and a 20 amino acid peptide (M. R. Price et al., Molec. Immunol., 27 795–802, 1990), which corresponds to a repeated motif in human MUC1 mucin (tumour-associated polymorphic epithelial mucin or PEM) (S. Gendler et al., J. Biol. Chem., 263:12820–12823, 1988; J. R. Gum et al., Biochem. Biophys. Res. Commun. 171 407–415, 1990).

CEA (20 mg/ml) and rsCD4 (10 mg/ml) were coated on immunotubes overnight at room temperature in phosphate buffered saline. For the first two rounds of selection tubes were washed 10 times with PBS, 0.1% (v/v) TWEEN-20 (neutral detergent) and 10 times with PBS. For subsequent rounds of selection tubes were washed 20 times with PBS, 0.1% (v/v) TWEEN 20 (neutral detergent) and 20 times with PBS. Phage were eluted with 100 mM triethylamine as (Marks et al., 1991). Eluted phage (usually 10$^6$ to 10$^7$ transducing units) were used to infect E. coli TG1 cells. Approx. 10$^9$ infected bacteria were used as an inoculum for the next rescue. The library was subjected to 3 to 5 rounds of rescue and selection for each antigen.

For selection of phage binding to the MUC1 peptide, the peptide was coupled chemically to SEPHAROSE 4B (provided by M. R. Price). A 1 ml column was prepared, and phage was selected as described by McCafferty et al., 1990, (supra). Briefly, the SEPHAROSE-MUC1 column was washed with PBS containing 2% skimmed milk powder (MPBS) and the phage loaded in 1 ml of the same buffer. After washing the column successively with 10 ml volumes of MPBS, PBS pH 7.2, 50 mM Tris-HCl/500 mM NaCl pH 8.0, and 50mM Tris-HCl/500 mM NaCl pH 9.0, phage was eluted with 5 ml 100 mM triethylamine and neutralised with 0.5M sodium phosphate buffer pH 6.8. Five rounds of selection were carried out.

Screening and Sequencing of Clones

Single ampicillin resistant colonies from infection of E. coli TG1 with eluted phage, were screened either for binding of phage (Clackson, et al., 1991) or soluble ScFv fragments (Marks et al., 1991). Since the gene encoding the antibody fragment is linked to that encoding the phage coat protein by an amber codon, soluble fragments can be secreted from a non-suppressor strain of bacteria infected by the phage (Hoogenboom et al., 1991). The binding to antigen of soluble scFvs in bacterial supernatant was detected with the mouse mAb 9E10 (1 µg/ml), which recognises the C-terminal peptide tag (Munro and Pelham, Cell 46, 291–300, 1986), and peroxidase-conjugated anti-mouse Fc antibody (Sigma Chemicals, Poole, Dorset, UK), as described (Ward et al., 1989). Plates were coated with the antigens Fog1, TNFα, bovine thyroglobulin and rsCD4 as described for immuno tubes above, and with CEA at 5 mg/ml. A urine extract containing human polymorphic epithelial mucin (PEM) as used at a protein concentration of approximately 10 mg/ml.

The specificity of the isolated clones was checked by ELISA of the soluble scFv fragments using plates coated with various proteins. Plates were coated with the antigens Fog-1, TNFa, bovine thyroglobulin, rsCD4, CEA and PEM as described above. Other proteins were coated overnight at room temperature at a concentration of 1 mg/ml in PBS (cytochrome c [Sigma Chemicals, Poole, Dorset, UK]) or in 50 mM NaHC03, pH 9.6 (bovine serum albumin, turkey egg-white lysozyme, hen-egg-white lysozyme, hen ovalbumin, keyhole limpet haemocyanin [CalBiochem], chymotrypsinogen A, chicken egg-white trypsin inhibitor [Sigma Chemicals, Poole, Dorset, UK], chicken gamma globulin coupled to 4-hydroxy-3-nitrophenyl acetic acid. Clones found to give a positive ELISA signal were screened by PCR and 'fingerprinted' with the restriction enzyme BstNI as in (Marks et al., 1991, supra) to identify different clones. Examples of clones with different restriction patterns were selected and the heavy and light chains sequenced using a Sequenase kit (USB) or using a TAQ DyeDeoxy Terminator Cycle Sequencing kit (Applied Biosystems, Foster City, Calif., USA) and an Applied Biosystems 373 DNA sequencer.

Sequenced clones were further analysed using the program MacVetor 3.5 (IBI Kodak, New Haven, Conn.). The VH genes were compared to the 83 germline gene segments present in the VH directory compiled by Tomlinson et al. (J.Mol.Biol. 227 776–798, 1992). VL genes were compared with 34 published kappa germline gene segments and 13 published lambda gene segments. Regions of the V-genes encoded by PCR primers were not included in the analysis.

The Selected Human Antibody Fragments Show High Specificity Against Self-antigens After two to five rounds of selection, E. coli cells were infected with eluted phage and antibody fragments produced by individual clones were screened for binding by ELISA. Phage selected with the 20 amino acid MUC1 peptide (Price et al., 1990, supra), which corresponds to a repeated motif in human MUC1 mucin (tumour-associated polymorphic epithelial mucin or PEM) (Gendler et al., 1988, supra; Gum et al., 1990, supra), were screened for binding to human PEM and hence bind to both peptide and the protein. The V-genes of clones with binding activities were sequenced, and one clone identified for each antigen of CEA, PEM and rsCD4 (Table I). The appearance of only low numbers of clones binding to CEA, PEM and human recombinant soluble CD4 (rsCD4), even after several rounds of selection, may reflect the use of VCS-M13 (stratagene) as helper phage (instead of M13DgIII helper used for the other antigens). Populations of phage(mid) particles produced by rescue with M13DgIII (which cannot produce pIII) have higher average avidities than those produced by rescue with VCS-M13 (where the wild-type pIII encoded by the helper phage can compete with scFv-pIII fusions).

Figure 2A:
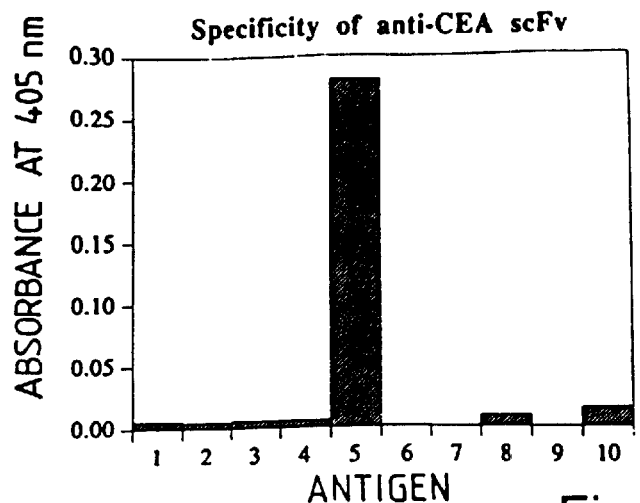
FIGS. 2A–2C show an analysis by ELISA of the specificities of soluble scFvs isolated from the unimmunised library by selection on human carcinoembryonic antigen (CEA)(A), the MUC1 peptide (Price et al., 1990, supra) (B), or human CD4 (C). Binding was determined by ELISA to a panel of proteins, as follows: 1—hen egg trypsin inhibitor; 2—chymotrypsinogen A; 3—hen egg ovalbumin; 4—keyhole limpet haemocyanin; 5—CEA; 6—urine extract containing human polymorphic epithelial mucin (PEM); 7—bovine thyroglobulin; 8—hen egg-white lysozyme; 9—bovine serum albumin; 10—chicken gamma globulin coupled to 4-hydroxy-3-nitrophenyl acetic acid; 11—human recombinant soluble CD4.
Figure 2B:
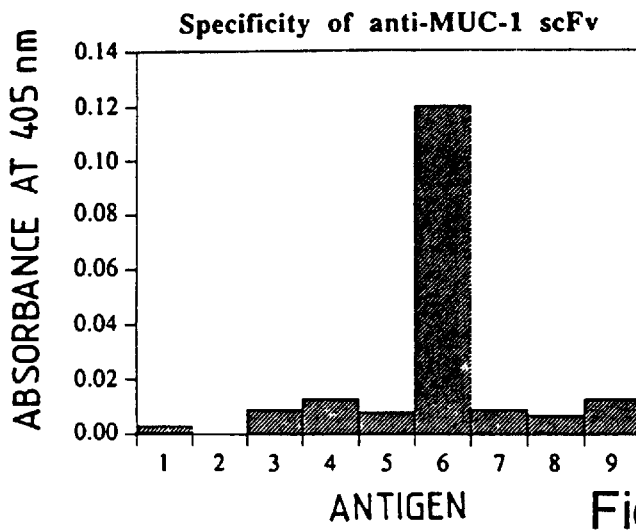
Figure 2C:
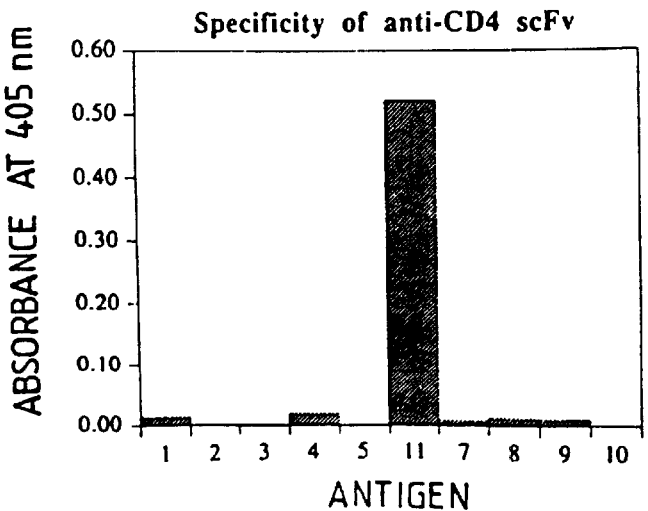

The scFv fragments were then screened for binding to a panel of other protein antigens, and were found to be highly specific. This is illustrated in FIG. 2A with the single clones with binding activity to human CEA, MUC1 and human rsCD4. See brief description of FIG. 2 (supra) for key.

Hence, antibody fragments directed against the human self antigens CEA and MUC1 (which are tumour markers) and rsCD4 can be derived from the same library and they all have a high specificity for antigen.

EXAMPLE 4

Characterisation of Antiself Antibody Fragments by DNA Sequencing and Binding to Antigen The antiself antibody fragments isolated in examples 1, 2 and 3 were characterized by DNA sequencing and antigen binding.

The Antibody Fragments are Derived from a Range of Unmutated and Somatically Mutated V-genes The sequences of several clones with self-specificity were determined as in examples 3 and contain both kappa and lambda light chains (Table II). Comparison with the sequences of the nearest germ-line V-gene segments indicates that several different families are used (VH1, 3, 4 and 5; Vk1 and 4, Vl1, 2 and 3). In a few cases the V-genes are completely germline, for example both the VH and Vl genes of aThy-29. However, most of the V-genes have several differences from the nearest germline V-gene segments, both at the nucleotide and amino-acid level (Table II), suggesting that they are derived from somatically mutated B-cells. Some mutations may have arisen during the POR amplification and assembly process, for example the VH-genes of aFOG1-G8 and aMUC1-1, and the Vk-gene of aThy-33 probably arose from cross-overs between two V-genes during PCR amplification (Table II). Furthermore, large differences (for example the Vk of aFOG1-H6 which differs by 36 nucleotides) may be due to the use of unknown V-gene segments. There is a striking homology in the CDR3 of the heavy chain between aTNF-A1 and aTNF-E1: the germline V-genes are different but the same JH segments are used, and 11/16 residues of CDR3 are identical. This suggests that both scFv fragments may bind to the same epitope of TNF.

The Antibody Fragments are Directed to Different Epitopes on the Same Protein

Figure 3A:
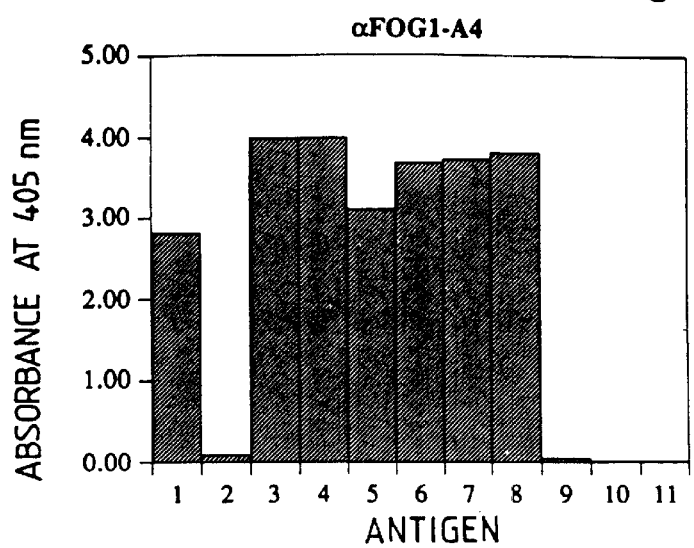
FIGS. 3A–3C show an ELISA to assay the binding of three scFvs, isolated by selection on a human monoclonal antibody Fog-1 (IgG1, kappa), to a panel of human antibodies of varying isotype, as follows: 1—Fog-1; 2—the Fv fragment of Hulys11; 3—Hulys11 antibody (IgG1, kappa); 4—RegA (IgG1, kappa); FogC (IgG3, kappa); 6—Pag1 (IgG1, lambda); 7 IgG2, lambda antibody purified from myeloma plasma (Sigma); 8—Oak3 (IgG3, lambda); 9—IgG04, lambda purified from myeloma plasma (Sigma); 10 Fom1 (IgM, lambda); 11—FomA (IgM, lambda).
Figure 3B:
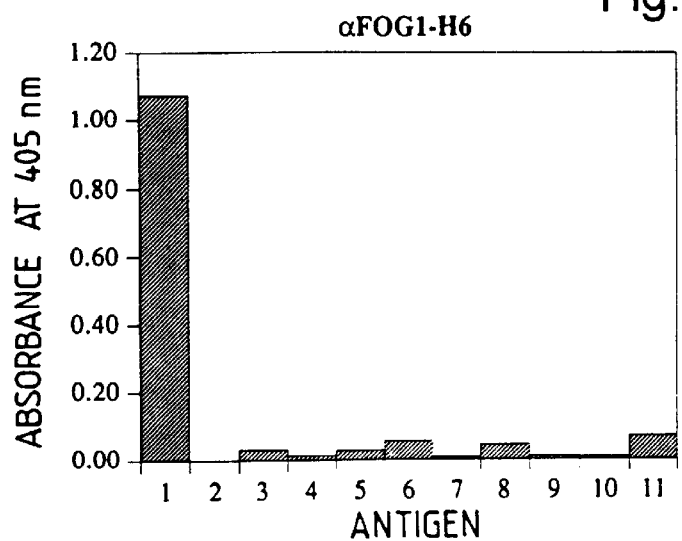
Figure 3C:
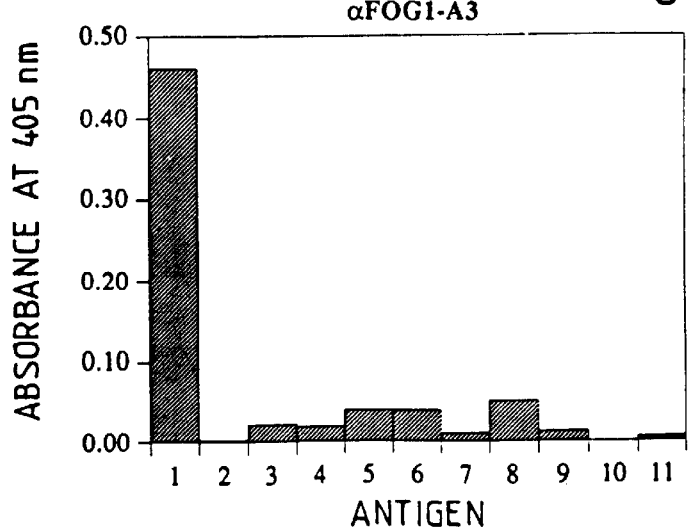

The scFv fragments directed against bovine thyroglobulin from example 2 were screened for binding to human thyroglobulin, which differs by only 6 single amino-acid residues in the protomer (Malthiery, Y. and Lissitzky, S. (1987) Eur. J. Biochem., 165, 491–498). Four of the twelve clones (including aThy-29) bound to human thyroglobulin, whereas the rest (including aThy-32 and aThy-33) did not (data not shown). Likewise the fragments binding to the human antibody Fog-1 were screened for binding to a range of other antibodies differing in heavy and light chain isotype (FIGS. 3A–3C). See brief description of FIGS. 3A–3C for its key (supra). The fragment aFOG1-A4 bound to all heavy chain g1, 2 and 3 isotypes, but not to g4 or m. By contrast, the fragments aFOG1-H6 and aFOG1-A3 did not bind to any of the other antibodies, including those of the same isotype as Fog-1, suggesting that they are directed to the variable domain of Fog-1.

Characterisation of Selected scFv Fragments

The following clones were chosen for large scale purification and further characterisation: aFOG1-H6, aFOG1-A3, aTNF-E7, and aThy-29. Colonies of the non-suppressor *E. coli* strain HB2151 harbouring the appropriate phagemid were used to inoculate 2 litres of 2×TY containing 100 μg ampicillin/ml and 0.1% glucose. The cultures were grown and induced (De Bellis, D. and Schwartz, I. (1990) Nucleic Acids Res., 18, 1311) and the tagged scFv fragments purified using the mAb 9E10 as in (Clackson et al., 1991, supra and WO92/01047).

The inhibition of 125I-Fog-1 binding to human Rh D antigen by the affinity purified scFv fragments aFOG1-H6 and aFOG1-A3 was essentially as performed earlier (Gorick, B. D., Thompson, K. M., Melamed, M. D. and Hughes, J. N. (1988) Vox. Sang., 55, 165–170) with the following modifications. 0.0148 μg of 125I-FOG1 was pre-incubated with varying amounts of purified aFOG1-H6 or aFOG1-A3 scFv fragments (0–16 μg) at 37° C. for 1.5 hours,. before adding 0.5 μl of R1R2 cells (or rr cells as control). The mixture was then incubated for a further 1.5 hours at 37° C. with constant mixing, and finally cells separated from the supernatant. As a control, a titration was also performed with a purified scFv fragment directed against turkey egg white lysozyme (aTEL9) (Marks et al., 1991, supra).

Kinetic measurements were made using surface plasmon resonance BIACORE (biosensor instrument, Pharmacia, Milton Keynes, UK) (Jönsson, U., Fgerstam, L., Invarsson, B., Lundh, K., Löfas, S., Persson, B., Roos, H., Rönnberg, I., Sjölander, S., Stenberg, E., Stahlberg, R., Urbaniczky, C., Östlin, H. and Maimqvist, M. (1991) BioTechniques, 11, 620–627, Jönsson, U. and Mamlqvist, M. (1992), In Turner, A. (ed.), Real Time Biospecific Interaction. JAI Press Ltd., San Diego, Vol. 2, pp. 291–336). In order to separate monomeric and multimeric species, the purified scFv fragments were concentrated by ultrafiltration and then fractionated on a calibrated SUPERDEX 75 FPLC column (Pharmacia, Milton Keynes, Herts, UK) in PBS, 0.2 mM EDTA. Gel filtration was monitored both by the absorbance at 280 nm and on-line to BIACORE (biosensor instrument, Pharmacia, Milton Keynes, UK) with immobilised antigen on the sensor chip (Johnsson et al., 1991).

Kinetic experiments were performed in two different configurations. First, to analyse the binding of soluble scFv, the different antigens were covalently immobilised on the sensor chip (in the case of mAb Fog-1, he antibody was also immobilised via a mouse anti-human kappa light chain mAb using a sensor chip coated with rabbit anti-mouse IgG1). Second, to analyse the binding of he soluble mAb FOG-1, the aFOG1-H6 scFv was immobilised on the chip surface.

The antigens were coupled to the CM5 sensor chip through their amine groups using the Amine Coupling Kit (Pharmacia Biosensor AB) Johnsson, B., Löfas, S., and Lindqvist. G. (1991) Anal. Biochem., 198, 268–277). The antigens were diluted in 10 mM acetate buffer pH 5.0 to approx. 25 μg/ml, and 3805 resonance units (RU) of TNF, 6249 RU of human thyroglobulin, and 5279 RU of FOG1 were immobilised. For the biospecific presentation of Fog-1, affinity purified rabbit anti-mouse IgG1 (Pharmacia Biosensor AB) was coupled to the surfaced followed by a mouse mAB anti-human kappa (2300 RU) and then Fog-1 (2050 RU). As binding of the rabbit anti-mouse IgG1 to the mouse mAB was reversible by 10 mM HCl the complex was rebuilt for each analytical cycle. ScFv anti-Fog-1 was coupled to the CM5 surface to 1538 RU. All determinations were performed at 25° C. in PBS, 0.2 mM EDTA, 0.05% BIA-CORE surfactant P20 (biosensor instrument, Pharmacia, Milton Keynes, UK) with a constant flow-rate of 10 μg/min. and an injected volume sample of 35 μl. It was not necessary to regenerate the antigen as the scFv fragments rapidly dissociate, with the exception of the biospecific presentation of antigen via rabbit anti-mouse IgG1 which was regenerated with 10 mM HCl for 3 min.

Analyses of scFv monomer were performed in the concentration range 100–500 nM, and dimers in the range 40–200 nM except for the biospecifically presented Fog-1 where the concentration of dimeric scFv was 0.25–1.26 μM. Fog-1 was analysed on the aFOG1-H6 scFv surface in the concentration range 10–200 nm. All concentrations were calculated from U.V. absorption at 280 nm (assuming that 0.7 mg/ml scFv gives an A280=1 [Mach, H., Middaugh, C. R. and Lewis, R. V. (1992) Anal. Biochem., 200, 74–80], and that Mr of a scFv monomer is 30 kD and of a dimer is 60 kD). No correction was made for the fraction of active protein, and therefore the on-rates are an underestimate. The kinetic evaluation of data was performed according to (Karlsson, R., Michaelsson, A. and Mattsson, L. (1991) J. Immunol. Methods, 145, 229–240) and evaluated on the program Origin 1.1 (Microcal inc., Northampton, Mass., USA).

Two of the Antibody Fragments are Directed Against Idiotypes of Human mAb Fog-1

The binding of 125I-Fog-1 antibody to human red blood cells bearing the Rh D antigen could be inhibited by both aFOG1-H6 and aFOG1-A3 scFv fragments. Hence, both aFOG1-H6 and aFOG1-A3 are site-associated anti-idiotype antibodies, complexing with the antigen-binding site of Fog-1. The extent of inhibition of 125I-Fog-1 binding to the Rh D antigen (on human R1R2 red blood cells) was determined by titration with affinity purified aFOG1-H6 and aFOG1-A3 scFv fragments. (As control, no inhibition of 125I-Fog-1 binding was observed using a scFv fragment (aTEL9) (Marks et al., 1991, supra) directed against turkey egg white lysozyme). With the maximum of 16 $\mu$g scFv (1000 fold molar excess to 125I-Fog-1), the binding was inhibited by 14.2% (aFOG1-H6) and 20.9% (aFOG1-A3), suggesting that the affinities of these fragments for Fog-1 are much lower than the affinity of Fog-1 for the Rh D antigen (Ka=$2.2\times10^9$ M$^{-1}$) which binds monovalently (Gorick et al., 1988, supra). If 100% of the fragments are active, the affinities of the two fragments for binding to Fog-1 could be estimated as Ka=$3\times10^5$ M$^{-1}$ for aFOG1-H6 and $6\times10^5$ M$^{-1}$ for aFOG1-A3, and this is consistent with other kinetic measurements (see below and Table III).

The scFv Fragments can Form Both Monomers and Dimers in Solution

Soluble antibody fragments were purified from bacterial supernatants by affinity chromatography, by binding of the C-terminal peptide tag to the mAB 9E10. After ultrafiltration, the fragments were further purified by FPLC gel filtration (Pharmacia) on SUPERDEX 75 FPLC column (Pharmacia, Milton Keynes, Herts, UK), and detected on-line both by UV absorption (280 nm) and by binding to antigen immobilised on a sensor chip in BIACORE (Pharmacia Biosensor AB, biosensor instrument, Pharmacia, Milton Keynes, UK). This showed that the scFV fragments emerged in two peaks, corresponding in size to monomers and dimers. The dimers bind more strongly to the immobilised antigen than monomers due to their greater avidity of binding. The scFv dimers run as monomers on non-reducing SDS gels, and are therefore not linked by disulphide bonds. As two peaks are seen in gel-filtration, it appears that in this case the monomers and dimers do not interconvert rapidly. Presumably the dimers are scFv fragments interlocked through the flexible linker joining the heavy and light chains, or with the heavy chain of one scFv molecule associated with the light chain of the other. We note that antibody Fab fragments made in bacteria can also multimerize (unpublished data).

The scFv Fragments have Micromolar Affinities

The presence of both scFv monomers and dimers could lead to an overestimate of affinity of binding using solid phase methods. To determine the affinity and kinetics of binding of scFv fragments to the antigen coated chip using surface plasmon resonance, we therefore purified the fragments by gel filtration (Table III). For the dimers, the off-rate constants were determined as about $10^{-2}$ s$^{-1}$ and the on-rate constants for the scFv dimers as about $10^5$–$10^6$ M$^{-1}$ s$^{-1}$ (assuming the sample is completely active). In the case of aFOG1-H6, the antigen (the mAb Fog-1) was immobilised on the sensor chip in two ways, either directly or via a rabbit anti-mouse IgG1 antibody. The results were almost identical by either method (see Table III). However the active fraction of scFv fragments varies considerably and could lead to an underestimate of the on-rate (and affinity of binding); for example using fluorescence quench titration with several scFv fragments directed against phenyloxazolone we detected only 0.06 to 0.38 functional binding sites per scFv molecule (unpublished data). Indeed the on-rate constants calculated for the association of the aFOG1-H6 fragment and Fog-1 antibody depend on whether the antibody ($k_{on}$ $2.2\times10^5$ M$^{-1}$ s$^-$) or scFv fragment ($k_{on}$ $1.0\times10^6$ M$^{-1}$ s$^{-1}$) is immobilised on the sensor chip (Table III), indicating that the aFOG1-H6 fragment is less active than the Fog-1 antibody. For the scFv monomers, the binding signals were low and it was difficult to follow the kinetics of binding to the surface, except for the dissociation of the aThy-29 monomer ($k_{off}$=$2\times10^{-2}$ s$^{-1}$). However, the four fold stabilisation of the aThy-29 fragment dimer (see below), suggests that the off-rate constants of the other monomers are >$10^{-2}$ s$^{-1}$, perhaps $10^{-1}$ s$^{-1}$.

The greater stability of the scFv dimers on the sensor chip, compared to monomers, indicates that the dimers are bivalent. The scFv dimers are therefore analogous to the two heads of the antibody IgG (but with different spacing between the heads), and their binding avidities were estimated as about $10^7$ M$^{-1}$ from $k_{on}/k_{off}$ (Table III). The affinities of the monomers must be lower by virtue of their faster dissociation from the surface. For the aThy-29 monomer, and assuming that the on-rate constant is the same as for the dimer (Mason, D. W. and Williams, A. F. (1986) Kinetics of Antibody Reactions and the Analysis of Cell Surface Antigens. Blackwell Scientific, Oxford), we can estimate an affinity of about $3\times10^6$ M$^{-1}$. These affinities, calculated from the rate constants measured by surface plasmon resonance appear to be similar to those measured in solution by fluorescence quench techniques. For example the affinity of binding of the monomer scFv fragment aTEL9 (Marks et al., 1991) which binds to turkey lysozyme (and was derived from the same library) was estimated as $3.9\times10^7$ M$^{-1}$ using surface plasmon resonance (Table III), and as $1.2\times10^7$ M$^{-1}$ by fluorescence quench (Marks et al., 1991, supra).

The affinities of antibodies isolated are typical of antibodies from the mouse primary immune response (Foote, J. and Milstein, C. (1991) Nature, 352, 530–532). The kinetics of association of the antibody fragments to the protein self-antigens ($10^5$ to $10^6$ M$^{-1}$ s$^{-1}$) are also typical of previously characterised Ab-protein interactions. However the kinetics of dissociation ($10^{-2}$ s$^{-1}$) are relatively fast for Ab-protein interactions (but both rates are slow compared to many Ab-hapten interactions). At first sight, it is surprising that we can isolate scFv fragments with such fast off-rates, as one would not expect a "monomeric" phage to be retained on the solid support during washing. However, scFv fragments are displayed multivalently on the phage, especially using the M13DgIII helper phage, and some of the scFvs which tend to form dimers in solution, may also form dimers on phage. The multivalent interactions with antigen help retain the phage, allowing the encoded scFv phage to be isolated.

Random combinatorial V-gene repertoires derived from the mRNA of immunised animals are enriched for heavy or light chain V-genes encoding part of an antigen binding site and this facilitates the isolation of antigen-binding fragments using phage technology, although the combinations of V-genes of each B-lymphocyte appear to be largely destroyed. Antigen binding sites can also be generated de novo by the random combination of chains, as illustrated by the isolation of scFv fragments against foreign antigens from unimmunised human donors (Marks et al., 1991, supra).

"Natural autoantibodies", self-reactive antibodies isolated from healthy donors tend to be of low affinity and polyspecific and may well be produced by a discrete subset of B-cells, the internal activity set (Holmberg, D. and Coutinho, A. (1985) Immunol. Today, 6, 356–357), contributed in part by CD5+ B-cells (Casali,P. and Notkins, A. L. (1989) Annu. Rev. Immunol., 7, 513–535). In contrast, the anti-self scFv fragments we have made are highly specific in binding to antigen despite only having micromolar affinities. This is a surprising and valuable finding. Their affinities could presumably be improved in vitro, for example, the affinity of an scfv fragment for the hapten phenyloxazolone derived from the phage library (and, like the anti-self antibodies described here, with a relatively fast off-rate) was improved from $Ka=3.1 \times 10^6$ $M^{-1}$ to $9.1 \times 10^8$ $M^{-1}$ by chain shuffling (WO92/01047; Marks et al., 1992b, Biotechnology 10, 779–783, 1992). This would allow the creation of highly specific, high affinity human antibodies directed against self-antigens for use in human therapy.

EXAMPLE 5

Creation of a Synthetic Library

By display of antibody repertoires on the surface of filamentous phage and selection of the phage with antigen[1], we can mimic immune selection [2,3] and make human antibodies from the rearranged V-genes of unimmunised donors[4]. Human antibodies have now been made by synthesis from defined V-gene elements. A repertoire of 49 human germ line VH gene segments was rearranged in vitro by joining to a synthetic "D-segment" of five random amino acid residues and a J-segment, to create a synthetic third complementarity determining region (CDR) of eight residues. The rearranged $V_H$ genes were cloned with a human V1ambda3 light chain as single-chain Fv fragments for phage display. The library of $10^7$ phages was panned with a hapten 2-phenyl-oxazoi-5-one (phOx) conjugate to bovine serum albumen (BSA), and phage isolated that encoded fragments with specific binding activity to phOx-BSA, and with affinities t phOx-gamma-aminobutyric acid (phOx-GABA) in the micromolar range. Comparison of twenty one clones with unique sequences showed that the in vitro "immune response" to the hapten was largely restricted to the $V_H26$ segment ($V_H3$ family)[6] with an invariant aromatic residue (Tyr, Phe, Trp) at residue 98 of CDR3. The use a V-genes rearranged in vitro may allow the design of antibody libraries biased towards the binding of antigens of known structure, and the creation of therapeutic human antibodies with reduced immunogenicity.

Antibody variable domains consist of a β-sheet framework with three loops of hypervariable sequence or CDRs[5]. The loops create antigen binding sites of a variety of shapes, ranging from flat surfaces[7] to pockets[8]. For human heavy chains, the sequence diversity of the first two CDRs are encoded by a repertoire of about fifty germ line $V_H$ segments. (I. M. Tomlinson et al., supra). The third CDR is generated from the recombination of these segments with about thirty D and six J segments[9], and although its sequence is highly variable, it often includes a salt bridge from Asp101 of the loop to Arg94 of the framework[10]. The structures and lengths of the first two CDRs are restricted[10,11] but those of CDR3 differ greatly, with lengths ranging from 4 to 25 residues[5].

Figure 4:
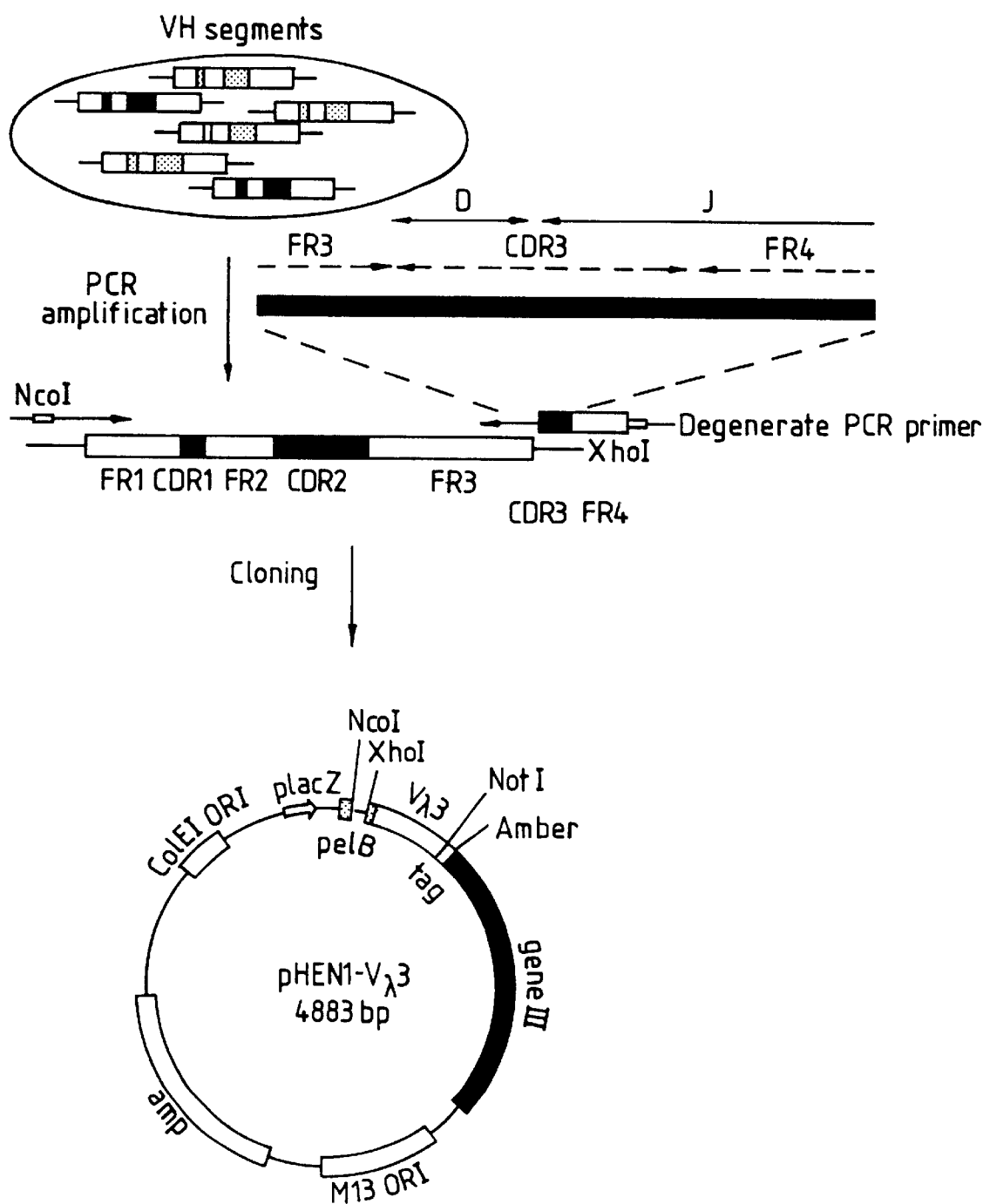
FIG. 4 illustrates the assembly of $V_H$ genes in the creation of a synthetic library.
Figure 5A:
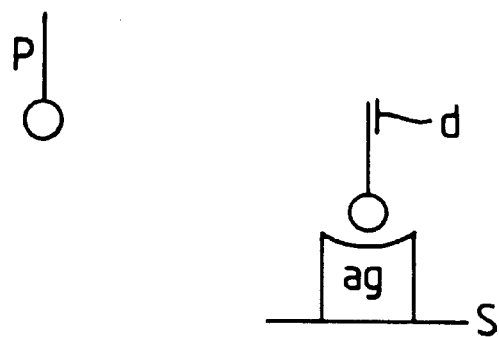
FIG. 5 shows schematically selection techniques for pAbs: 2(i) shows a binding/elution system; 2(ii) shows a competition system (p=pAb; ag=antigen to which binding by pAb is required; c=competitor population e.g. antibody, pAb, ligand; s=substrate (e.g. plastic beads etc); d=detection system).
Figure 5B:
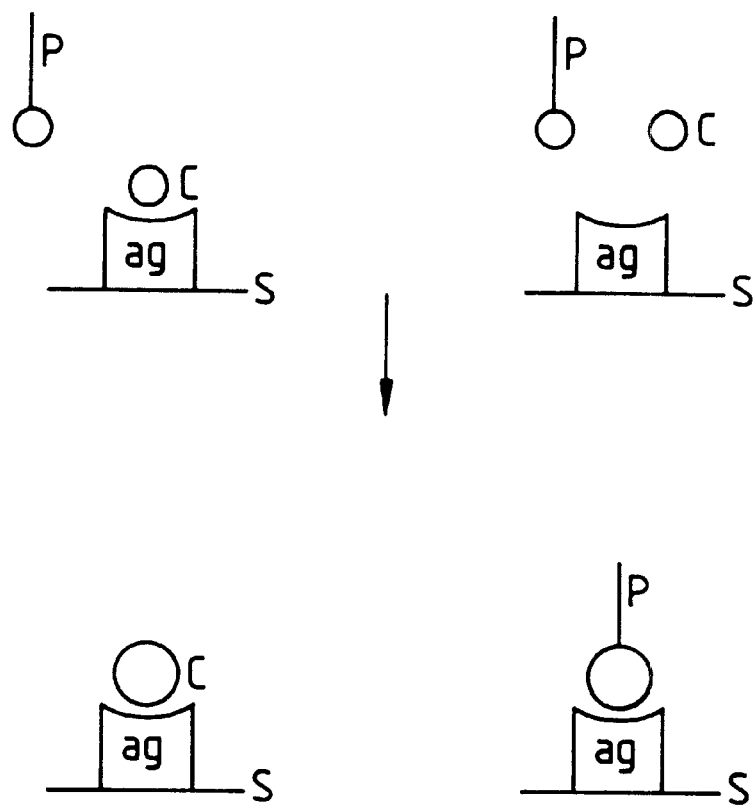

A library was created of rearranged $V_H$ genes with a CDR3 of eight residues including Asp101, in combination with a single Vlambda (ref.12) light chain. Forty nine germ line $V_H$ segments encoding most of the human $V_H$ repertoire (Tomlinson et al., supra) were each amplified using the polymerase chain reaction[13] and oligonucleotide primers that introduce a synthetic D-segment (of 15 bases of random sequence at the 3' end of the $V_H$ segment) and a J-segment, together encoding a CDR3 loop of eight residues (FIG. 4). The rearranged segments were pooled and cloned for phage display with a human V1ambda3 light chain, creating a synthetic library of $10^7$ phage clones. Like the immune system, the synthetic library of $10^7$ phage clones can tap only a small fraction of the potential diversity. Thus the diversity is potentially $49 \times 32^5 = 1.6 \times 10^9$ different nucleotide sequences, or $49 \times 20^5 = 1.6 \times 10^8$ different amino acid sequences.

The library was subjected to four rounds of growth and panning on phox-bovine serum albumin (BSA) coated tubes, and clones screened as soluble[14] single chain Fv fragments[15,16] for binding activity to phOx-BSA by ELISA[4]. After the third and fourth rounds, 14/96 and 61/96 clones respectively were identified with binding activities to phOx-BSA and of these (29 tested) none bound to other proteins (see legend Table B). Furthermore their binding to phOx-BSA coated plates could be competed with the soluble hapten (Table B).

Sequencing revealed that many (21/29) of the phox binders were unique, with an eight residue CDR3, and utilised either a segment from the $V_H4$ family, or one of three segments from the $V_H3$ family (Table B). Together these segments use three of the seven "canonical" folds available to the first two hypervariable loops of human $V_H$ segments. (C. Chothia, et al., supra). The majority of the unique clones (16/21) were derived from the VH26 segment[6] and have related sequences in the third hypervariable loop: in this group the first residue tends to have a branched aliphatic side chain (15/16), the second residue tends to be lysine or arginine (11/16), while the fourth residue is always an aromatic residue (most frequently tyrosine).

The affinities (Kd) of two of the stronger binders (Ox 13 and Ox-31, Table B) for phOx-GABA were determined by fluorescence quench titration[17] as $3.1 \pm 0.2$ μM and $6.7 \pm 0.7$ μM respectively. Although the synthetic antibody library lacks the diverse VH-CDR3 lengths and the different light chains of antibodies made in vivo, the affinities for phOx-GABA compare with 0.5 μM for a (phage) antibody made from unimmunised human donors[4], or 1μM for several hybridomas from a mouse primary immune response[18] (but see caveat, Table A legend). To improve these affinities, one could systematically alter (see below) the many different phOx antibodies selected (Table A).

In principle, the use of phage display libraries of V-genes rearranged in vitro offers an attractive alternative to those rearranged in vivo[4]. Firstly the framework regions and first two hypervariable loops of both heavy and light chains of the synthetic human antibodies created from he library are essentially germ line. This contrasts with the "primary" phage antibodies tapped from human V-genes rearranged in vivo, in which the extent of somatic mutation varied widely[4]. Leaving aside polymorphism, the VH gene segments are identical in different individuals, and the synthetic antibodies are potentially less immunogenic. By altering the lengths and sequences of the heavy and light chain CDR3 loops, or by localising the minimal mutations in the other CDR loops, or by shuffling with synthetic "germ line" light chains[19,20], it may be possible to improve their affinities while retaining their germ line character.

Secondly both kinds of libraries are highly biased. In the "natural" libraries, the bias is outside our control, and is imposed for example by allelic variation, deletion polymorphism and deletion of self-reactive clones. In the synthetic library, the bias can be introduced systematically. Here for example, all the VH-gene segments, were chosen and thereby the folding of the first and second hypervariable loops: also fixed were the length and diversity of VH-CDR3 and the light chain. Although several ways of making diverse synthetic libraries hare been suggested[2], it should also be possible to incorporate design principles into the encoded structures. If the shape of the antigen were known, an envelope of roughly complementary binding sites might be designed and built with defined V-gene elements. Use of such "designer" libraries would favour the isolation of antibodies with higher affinities.

TABLE A

| Family | No. of genes | VH segments* | Library size × $10^{-6}$ (%) |
|---|---|---|---|
| $V_H1$ | 14 | 1–5,7,8,10,12, 14,15,20,21,25 | 2.3 (20) |
| $V_H2$ | 1 | 27 | 1.0 (9) |
| $V_H3$ | 23 | 29–33,35,38–40, 42,44–54,58,59 | 2.1 (19) |
| $V_H4$ | 9 | 63–71 | 2.6 (23) |
| $V_H5$ | 1 | 73 | 1.4 (12) |
| $V_H6$ | 1 | 74 | 1.9 (17) |
| Total: | 49 | | 11.3 (100) |

*for simplicity $V_H$ segments are listed according to DP nomenclature of Tomlinson et al., supra.

Table A—Composition of the Synthetic Library

Forty nine human $V_H$ segments (Tomlinson et al, supra) were used, one for each of the $V_H2$, $V_H5$ and $V_H6$ gene families and multiple segments for the other three families, and cloned according to family. Clones from the $V_H$ segments of each family were checked for presence of insert (on average 85%) and pooled into a single large library as in Table B, creating a (controlled) bias for certain gene families. The segments from the $V_H2$, $V_H5$, $V_H6$ families are thereby "overrepresented" with respect to the segments from other families. Sequencing of thirty five clones from the unselected library confirmed that $V_H$ segments from each family were present, and that the nucleotides were present in the expected ratios in the D-segment, but with a slight bias, for C. (A the first and second position of each codon, A, 21.3%; G, 17.9%; C33.7% and T, 27.1%; at the third position, G, 42.6% and T, 57.4%). The expression levels of the antibody fragments were also checked, and $V_H$ segments were identified in clones with detectable expression levels, for example $V_H1$ (DP-7), $V_H2$ (DP-27), $V_H3$ (DP-29, 35, 38, 44, 47, 51, 53), $V_H4$ (DP-63,69), $V_H5$ (DP-73) and $V_H6$ (DP-74).

Methods

The clones were checked for presence of insert by 'PCR-screening'[21] with oligonucleotides LMB3 and pHEN-SEQ (ref.4) and sequenced from double-stranded DNA by the dideoxy chain termination method[22] with oligonucleotide LINKSEQ (SEQ ID NO.:21) (5'-CGA TCC GCC ACC GCC AGA G-3'). (The numbers in the tables are corrected for insert). Expression of soluble scFv fragments was checked by spotting 10 μl supernatant of induced overnight cultures in E. coli HB2151 (ref.14) onto a nitrocellulose filter using a slot-blot device (Minifold II, Schleicher and Schuell), and detecting the bound peptide-tagged scFv fragments with 9E10 antibody[23] and peroxidase labelled anti-mouse antibodies (Sigma Chemicals, Poole, Dorset, UK).

TABLE B

| Clone | Family | Germline gene* | Canonical Loop structure* | $I_{50}^{\phi}$ |
|---|---|---|---|---|
| Ox-31 | $V_H3$ | DP-42 | 1-1 | 26 |
| Ox-15 | $V_H3$ | DP-45 | 1-1 | >300 |
| Ox-18 | " | " | " | >300 |
| Ox-33 | $V_H3$ | DP-47 | 1-3 | 20 |
| Ox-13 | " | " | " | 50 |
| Ox-9 | " | " | " | 80 |
| Ox-7 | " | " | " | 86 |
| Ox-30 | " | " | " | 86 |
| Ox-12 | " | " | " | 86 |
| Ox-5 | " | " | " | 100 |
| Ox-3 | " | " | " | 125 |
| Ox-20 | " | " | " | 125 |
| Ox-21 | " | " | " | 125 |
| Ox-4 | " | " | " | 130 |
| Ox-10 | " | " | " | 150 |
| Ox-14 | " | " | " | 180 |
| Ox-19 | " | " | " | 250 |
| Ox-25 | " | " | " | >400 |
| Ox-27 | " | " | " | ¶ |
| Ox-2§ | $V_H4$ | DP-67 | 2-1 | >400 |
| Ox-1 | " | " | " | >400 |

*Tomlinson et al., supra, Chothia et al., supra.
$^{\phi}$in μM, according to competition ELISA with phOx-GABA.
§shows V67A mutation in FR3.
¶Not determined.

Table B—phOx-binders Isolated from the Synthetic Library

Phage were prepared from the library by rescue with VCS-M13, and subjected to rounds of panning in phOx-BSA coated tubes as in ref.4. The sequences of 21 phage binding to phOx revealed four germ line VH segments, DP-42,45,47 (VH3 family) and DP-67 (VH4 family). DP-47 is identical to VH26 (ref.6, corrected in ref.24), while DP-42, DP-45 and DP-67 only differ in one or a few framework residues from 8-1B (ref.25), 65-2 (ref.26) or VH4.22 (ref.27) respectively. Clones from the unselected library using the DP47 $V_H$ segment and lacking the characteristic pattern of CDR3 did not bind to phOx. Of the 21 phOx binders tested, none bound to BSA, NIP-BSA, plastic, chymotrypsinogen A, cytochrome c, bovine thyroglobulin, keyhole limpet haemocyanin or turkey egg white lysozyme. Four clones that bound to BSA (but not to phOx) were found on be contaminants (αBSA3 clones, from ref.4).

Methods

As in ref.4. The relative affinities of the scFv fragments were determined by inhibition ELISA[28]. A serial dilution of 4-gamma-amino-butyric acid methylene 2-phenyl-oxazol-5-one (phOx-GABA), with concentrations ranging from 6 to 400μM., was made in 4% Marvel-PBS, and scFv supernatant added. The concentration of phOx-GABA resulting in a 50% reduction of the signal ($I_{50}$) for binding to phOx-BSA was noted. The affinities of the clones Ox-13 and Ox-31 for phOx-GABA were determined by fluorescence quench titration using scFv purified by the c-myc tag (ref.4). Ideally, the affinity for the phOx-BSA conjugate would have been measured directly, or that for phOx-caproic acid, but phOx-GABA was used here to allow comparison with the hybridoma data of ref.18. The affinities of the antibodies for the phOx conjugate, or for phOx-caproic acid are likely to be better than those measured for phox-GABA.

FIG. 4—Shows the Assembly of Rearranged VH Genes (See Text)

Methods

A synthetic oligonucleotide SYNLIB1 (see (SEQ ID NO.:1) Table IV) introduced a D-segment with a five residue random amino acid sequence, a J-segment and an XhoI restriction site, to the 3' end of each of 49 human $V_H$ germline segments (Tomlinson et al., supra). The primer was used in the polymerase chain reaction[13] with a $V_H$ family based back primers (VHBACK) incorporating an NcoI site[4], HuVH1BackSfi (SEQ ID NO.:15) to HuVH6BackSfi (SEQ ID NO.: 20). Each VH segment clone (provided as single stranded template in M13 vector) was amplified separately at 94° C. for 1 min, 50° C. for 1 min, and 72° C. for 1.5 min, for 25 cycles, on a PHC-3 thermocycler (Techne, Cambridge, UK). Each amplification was checked by electrophoresis on agarose gel, and similar amounts of DNA from $V_H$ segments of the same family were pooled, digested with NcoI and XhoI, and cloned into the vector pHEN1 (ref. 14) carrying a rearranged V1ambda3 light chain variable domain (IGLV3SI; ref.12) taken from a scFv fragment binding to BSA[4].

If, instead of a random oligonucleotide, an oligonucleotide encoding a CDR, eg from a rodent, were used, this would imprint that non-human CDR on the product synthetic human library.

References Mentioned in Example 5

1. McCafferty, J., Griffiths, A. D., Winter, G. & Chiswell D. J. (1990). *Nature*, 348, 552–554.
2. Milstein, C. (1990). *Proc R Soc Lond Biol*, 239, 1–16.
3. Winter, G. & Milstein, C (1991). *Nature*, 349, 293–299.
4. Marks, J. D., et al (1991). *J Mol Biol*, 222, 581–597.
5. Kabat, E. A., T. T., Reid-Miller, M., Perry, H. M. & Gottesman, *Sequences of proteins of immunological interests* (US Department of Health and, Human Services, US Government Printing Office, 1987).
6. Matthyssens, C. & Rabbits, T. H. (1980). *Proc Natl Acad Sci USA*, 77, 6561–6565.
7. Amit, A. G., Mariuzza, R. A., Phillips, S. E. & Poljak, P. J. (1986). *Science*, 233, 747–753.
8. Alzari, P. M, et al (1990). *Embo J*, 9, 3807–3814.
9. Ichihara, Y., Matsuoka, H. & Kurosawa, Y (1988). *Embo J*, 7, 2141–4150.
10. Chothia, C. & Lesk, A. M. (1987). *J Mol Biol*, 196, 901–917.
11. Chothia, C., et al (1989). *Nature*, 342, 877–883.
12. Frippiat, J. P., et al (1990). *Nucleic Acids Res*, 18, 7134.
13. Saiki, R. K., et al (1985). *Science*, 230, 1350–1354.
14. Hoogenboom, H. R., et al (1991). *Nucleic Acids Res*, 19, 4133–4137.
15. Huston, J. S., et al (1988). *Proc Natl Acad Sci USA*, 85, 5879–5883.
16. Bird, R.E., et al (1988). *Science*, 242, 423–426.
17. Eisen, H. N. (1964). *Meth Med Research*, 10, 115–121.
18. Foote, J. & Milstein, C. (1991). *Nature*, 352, 530–532.
19. Clackson, T., Hoogenboom, H. R., Griffiths, A. D. & Winter, G (1991). *Nature*, 352, 624–628.
20. Roberts, A. J., et al (1992). *Bio/Technology*, in press.
21. Gussow, D. & Clackson, T. (1989). *Nucleic Acids Res*, 17, 4000.
22. Sanger, F., Nicklen, S. & Coulson, A.R. (1977). *Proc Natl Acad Sci USA*, 74, 5463–5467.
23. Munro, S. & Pelham, H. R. B. (1986). *Cell*, 46, 291–300.
24. Chen, P. P., Liu, M. F., Sinha, S. & Carson, D. A. (1988). *Arthritis Rheum*, 31, 1429–1431.
25. Berman, J. E., et al (1988). *Embo J*, 7, 727–738.
26. Matsuda, F., et al (1990). *Embo J*, 9, 2501–2506.
27. Sanz, I., et al (1989). *Embo J*, 8, 3741–3748.
28. Rath, S., Stanley, C. M. & Steward, M. W. (1988). *J Immunol Methods*, 106, 245–249.

EXAMPLE 6

Isolation of Antibody Fragments Specific for Tumour Necrosis Factor-a from a Germ Line Human Synthetic Library A clone encoding an antibody fragment specific for tumour necrosis factor-α was isolated from a germ line human synthetic library. This library was prepared as described in example 5, except that the oligonucleotide SYNLIB2 (SEQ ID NO.: 2) was used in place of SYNLIB1 (SEQ ID NO.: 1), so that a 5 amino acid $V_H$ CDR3 was generated. The library was panned against tumour necrosis factor-α, as described in example 1 for the library derived from unimmunised humans. After four rounds of panning a phage antibody (and corresponding soluble fragment) was isolated with binding activity to TNF. The $V_H$ region of the scFv fragment (αTNF-10) was derived from the VH segment DP-45 (Tomlinson et al, 1992, supra). The hapten binding clones αNIP-6, αNIP-12, αOx-15 and αOx-18 are also derived from this segment, although each of these fragments were nevertheless specific for binding to hapten or TNF. This indicates that antigen binding sites with entirely different specificities can be created on the same antibody framework by substitution of CDR3 alone. Binding to non-specific antigens was assessed by ELISA as described in example 1.

EXAMPLE 7

Isolation of Single Chain Fv Fragments Binding to Human Thyroalobulin and a Human Monoclonal Antibody from a Germ Line Human Synthetic Library Containing VH CDR3 Sequences of Different Lengths A germ line human synthetic single chain Fv fragment library was prepared in an analagous manner to the library in Example 5, to include germ line VH segments and synthetic DH and JH regions, generating Vt: CDR3 regions of between 4 and 12 amino acids. A single germ line rearranged light chain was provided. This phage library has been used as a source of antibody fragments with anti-human specificities.

Fifty germ line gene VH segments (Tomlinson et al, 1991 supra, as in Example 5) were amplified with oligonucleotides to introduce a completely randomised CDR3 varying in length from 4 to 12 residues. In a first PCR-reaction, each gene was amplified with its family specific VHBACK-primer (one of VH1BACKSfi to VH6BACKSfi; Marks et al, 1991 supra; WO92/01047) at the 5' end, and, annealing at the 3' end, one of each of the oligonucleotides of the series SYNLIB4–SYNLIB12 (SEQ ID NOS.; 3–11) (Table IV). The PCR contained 2.5 pmol of each of the appropriate pair of oligonucleotides per 50 µl reaction mix containing 250 µM dNTPs, 10 mM KCl, 10 mM $(NH4)_2SO_4$, 20 mM TrisHCl (pH8.8), 2 mM MgC12, 100 µg/ml BSA and 1 µl (1 unit) of TAQ DNA polymerase (Cetus/Perkin Elmer, Beaconsfield, Bucks, UK). The template was 1 µl of a bacterial stock of *E. coli* infected with a M13 phage clone encoding the appropriate germ line V gene. The amplification cycle was 94° C. for 1 min, 55° C. for 1 min and 72° C. for 1.5 min. After 25 cycles, 30 pmol of the same VHBACK oligonucleotide and 30 pmol of JHSAL (SEQ ID NO. 12) (Table IV) was added, and the PCR continued for 15 cycles, introducing a SalI cloning site at the 3' end of the VH-gene. After verifying that a band of the appropriate size was seen on agarose gel electrophoresis, the PCR products of all amplifications done with the same SYNLIB primer were collected, cut with NcoI and SalI, and cloned into NcoI-XhoI-cut pHEN1-V 3 (pHEN1 containing cloned IGLV3S1) as in Example 5. In this way, 9 libraries (each with one particular CDR3 length) were made, each containing between $5 \times 10^6$ and $5 \times 10^7$ clones.

Selection

Phage was prepared from the nine different libraries by rescue with VCS-M13 as described in Example 3. Phage from the nine individual libraries was mixed to give one large library and subjected to panning on one of each of 2 antigens: Immunosorp tubes were coated with OAK3 (human anti-Rhesus D antibody, IgG3, k) overnight in carbonate buffer (0.1 M NaHCO$_3$, pH 9.6 at 100 µg/ml) or human thyroglobulin (coated at 100 µg/ml in PBS). Selections were performed as in Example 3.

Screening

ELISA was performed as described in Hoogenboom et al, 1991 supra. ELISA plates were coated overnight with OAK3 at 100 µg/ml in PBS at room temperature or with human thyroglobulin at 100 µg/ml at room temperature.

Results

After four rounds of selection on OAK3-coated tubes, eluted phage was used to infect HB2151, and soluble scFv fragments analysed for binding by ELISA. 59/96 clones were scored positive in the OAK3 ELISA.

The germ line human synthetic library was also subjected to: 5 rounds of selection on human thyroglobulin coated tubes, 80/96 clones were found to be positive in a phage ELISA of individual clones rescued with VCS-M13.

Two of each of the positive clones were analysed in ELISA for binding against a range of antigens (OAK3, human thyroglobulin, phOx-BSA, NIP-BSA, BSA, ovalbumin, chymotrypsinogen-A, streptavidin, cytochrome c, KLH, turkey egg-white lysozyme). The two OAK-3-binding clones (as soluble scFv fragments) both gave signals approximately 3-fold higher than background in ELISA on OAK3. The two thyroglobulin binding clones (as sc:Fv fragments displayed on phage) both gave signals approximately 5-fold higher than background in thyroglobulin-ELISA. All the clones were found to be highly specific for the antigen against which they had been selected. By hybridisation to family-specific primers (J. D. Marks et al, Eur. J. Immunol. 21 985–991 1991), the VH segment of all four clones was identified to be of the VH3 family. The CDR3 length of each clone was analysed by amplifying the CDR3 with oligonucleotides CDRFOR (SEQ ID NO.: 13) and CDRBACK (SEQ ID NO.: 14) (Table IV), and analysing the product on an 8% polyacrylamide gel. For the two OAK3-binding clones, we found a length of 4 or 7 amino acid residues, while the thyroglobulin binding clones both use a CDR3 length of 10 residues.

Hence, antibody scFv fragments binding to a human monoclonal antibody and a human self antigen have been isolated from a human germ line synthetic library.

EXAMPLE 8

Isolation of Antibody Fragments Triggering the Activity of the Interleukin-1 Receptor The library of single chain Fv fragments derived from an unimmunised human that was described in Example 1 is used to select antibodies which will trigger the activity of the interleukin-1 receptor. Antibody fragments are first isolated which bind to the soluble external domain of the interleukin-1 receptor (IL-1R) of T cells. Antibody clones that are thus identified are then analysed in assays for interleukin-1 type biological activity. The IL-1R on murine and human T cells is a highly homologous 80 kD cell surface glycoprotein which binds both interleukin-1α and interleukin-1β. A cDNA clone encoding the N terminal 316 amino acids of the murine receptor external domain has been expressed in HeLa cells (S. K. Dower et al. J. Immunol. 142 4314–4320 1989). The soluble IL1-R molecule thus expressed has been purified and shows binding properties indistinguishable from the full length IL-1R molecule, a complex being formed between a single soluble IL1-R molecule and IL-1. This soluble receptor molecule binds to human interleukin-1. The human T cell interleukin 1 receptor has been cloned and sequenced by J. E. Sims et al (Proc. Natl. Acad. Sci. USA 86 8946–8950, 1989). The soluble external domain of the human IL1 receptor, amino acids 1 to 316, is expressed in HeLa cells and purified as described for the murine receptor.

The rescued unimmunised human library is first selected against the recombinant human soluble IL-1 receptor, corresponding to the external domain of the IL-1 receptor. Immunotubes are coated with the soluble IL-1 receptor as described in Example 1 at 10 µg/ml and panning is performed as described in Example 1 for a total of four rounds of affinity selection.

Clones binding to soluble IL-1 receptor are characterised by ELISA using microtitre plates coated with recombinant soluble L-1 receptor at 10 µg/ml as described for TNF-α in Example 3. Antibody fragments showing significant ELISA signals with soluble IL-1 receptor but not with non-specific antigens are then chosen for further study.

Antibody clones isolated in this way are then expressed as soluble scFv fragments in *E. Coli* and purified as described in Example 4 by mAb 9E10 affinity chromatography. Binding to human receptors is assessed using binding of $^{125}$I-labelled antibody fragment to human fibroblast cell line TIG-1 expressing the interleukin-1 receptor basically as described by T. Takii et al (Eur. J. Immunol. 22 1221–1227 1992) for determining the affinity of $^{125}$I,-IL1c for the receptor on these cell lines. The purified antibody fragments that show receptor binding are used in a biological screening assay using human epithelial cells to examine them for stimulation of synthesis of prostacyclin (PGI2) and platelet activating factor (PAF) as described by E. Dejana et al (Blood 69 695–699, 1987). These studies will identify antibody -fragments which have an antiself specificity against.

IL-1 receptor which triggers receptor activity. The activity can be quantified relative to human interleukin-1α using a standard bioassay for IL-1α for example proliferation of the D1OS helper T cell line using $^3$H-thymidine incorporation (S. F. Orencole and C. A. Dinarello Cytokine 1 14–22 1989) or a conversion proliferation assay as described by A. J. Gearing et al (J. Immunol. Methods 99 7–11, 1987).

TABLE I

Frequency of binding clones isolated from the unimmunised scFv library after selection

| | Rounds of selection | | | | | No. of unique |
|---|---|---|---|---|---|---|
| Antigen | 1 | 2 | 3 | 4 | 5 | clones |
| Thyroglobulin (bovine) | — | — | 18/40 | — | — | 12 |
| Thyroglobulin (human): selected on bovine | — | — | 10/40 | — | — | 4 |
| Fogl (human IgGl, k antibody) | — | — | — | 94/96 | — | 4 |
| TNFα (human) | — | 122/1920 | 83/192 | 92/96 | — | 7 |
| CEA (human) | — | — | 0/96 | 1/96 | 2/96 | 1 |
| MUC1 (human): selected with peptide | — | — | — | 0/96 | 2/96 | 1 |
| rsCD4 (human) | — | — | — | — | 8/96 | 1 |

The ratios indicate the frequency of binding clones after each round of selection. Phagemids were rescued with M13DgIII helper phage, except for the CEA, MUC1 and rsCD4 selections, where VCS-M13 helper phage was used.

TABLE II

V-gene family, germline derivation and extent of
somatic hypermutation of several antigen-specific
scFv fragments isolated from the unimmunised library

| scFv | Family | Germline gene of closest nucleotide sequence | Differences from germline Nucleotide | Amino-acid |
|---|---|---|---|---|
| HEAVY CHAINS | | | | |
| αThy-23 | VH3 | DP-47 | 13 | 8 |
| αThy-29 | VH1 | DP-14 | 0 | 0 |
| αThy-32 | VH3 | DP-31 | 5 | 2 |
| αThy-33 | VH3 | DP-49 | 32 | 19 |
| αFOG1-A3 | VH3 | DP-54 | 7 | 3 |
| αFOG-A4 | VH3 | DP-46 | 7 | 7 |
| αFOG1-H6 | VH3 | DP-51 | 10 | 4 |
| αFOG1-G8[a)] | VH4 | DP-63 (FR1) | 2 | 0 |
| | VH5 | DP-73 (CDR1 to FR3) | 15 | 7 |
| αTNF-A1 | VH3 | DP-50 | 9 | 6 |
| αTNF-F1 | VH3 | DP-46 | 14 | 6 |
| αTNF-E7 | VH1 | DP-10 | 0 | 0 |
| αTNF-H9G1 | VH1 | DP-4 | 1 | 1 |
| αCEA4-8A | VH1 | DP-14 | 1 | 0 |
| αMUC1-1[a)] | VH1 | VI-2 (FR1 to CDR2) | 2 | 0 |
| | VH1 | DP-25 (FR3) | 0 | 0 |
| αCD4-74 | VH5 | DP-73 | 13 | 8 |
| LIGHT CHAINS | | | | |
| αThy-23 | Vk1 | L8 | 20 | 9 |
| αThy-29 | Vλ3 | IGLV3S1 | 0 | 0 |
| αThy-32 | Vλ1 | IGLV1S2 | 1 | 1 |
| αThy-33[a)] | Vk1 | L12 (FR1 & CDR1) | 6 | 3 |
| | Vk4 | B3 (FR2 to FR3) | 5 | 5 |
| αFOG1-A3 | Vλ2 | VL2.1 | 16 | 9 |
| αFOG1-A4 | Vk1 | O4 | 25 | 12 |
| αFOG1-H6 | Vk1 | L5 | 36 | 17 |
| αFOG1-G8 | Vk1 | L8 | 27 | 14 |
| αTNF-A1 | Vk1 | L11 | 12 | 8 |
| αTNF-E1 | Vk1 | L5 | 5 | 5 |
| αTNF-E7 | Vk1 | L11 | 17 | 8 |
| αTNF-H9G1 | Vλ1 | IGLV1S2 | 18 | 9 |
| αCEA4-8A | Vk1 | O2 | 4 | 0 |
| αMUC1-1 | Vλ2 | VL2.1 | 18 | 12 |
| αCD4-74 | Vλ1 | Hum1v1L1 | 23 | 17 |

References for all the heavy chain germline genes can be found in Tomlinson et al. (1992). The references for the light chains are VL2.1 (Brockly et al. 1989); IGLV1S2 (Bernard et al. 1990); IGLV3S1 (Frippiat et al. 1990); L8(Vd) and L5(Vb) (Pech et al., 1984); L12(HK102) (Bentley and Rabbits, 1980); B3(VKIV) (Klobeck et al., 1985); 02 and 04 (Pargent et al., 1991); L11 (Scott et al., 1991); Hum1v1L1 (Daley et al., 1992). Alternative names are given in parenthesis.

a) These genes appear to have been created by cross-overs between two V-genes during PCR amplification and therefore matches have been determined using the two putative germline segments: FR, framework; CDR, complementarity-determining region.

Bentley, D. L. and Rabbits, T. H. (1980) *Nature*, 288, 730–3.

Bernard, F., Chuchana, P., Frippiat, J. P., Buluwela, L. and Lefranc, M. P. (1990) *Nucleic Acids Res*, 18, 7139.

Brockly, F., Alexandre, D., Chuchana, P., Huck, S., Lefranc, G. and Lefranc, M. P. (1989) *Nucleic Acids Res*, 17, 3976.

Frippiat, J. P., Chuchana, P., Bernard, F., Buluwela, L., Lefranc, G. and Lefranc, M. P. (1990) *Nucleic Acids Res*, 18, 7134.

Klobeck, H. G. Bornkamm, G. W., Combriato, G., Mocikat, R.,

Pohlenz, H. D. and Zachau, H. G. (1985) *Nucleic Acids Res*, 13, 6515–29.

Pargent, W., Meindl, A., Thiebe, R., Mitzel, S. and Zachau, H. G. (1991) *Eur J Immunol*, 21, 1821–7.

Pech, M., Jaenichen, H. R., Pohlenz, H. D., Neumaier, P. S., Klobeck, H. G. and Zachau, (1984) *J Mol Biol*, 176, 189–204.

Scott, M. G., Crimmins, D. L., McCourt, D. W., Chung, G., Schable, K. F., Thiebe, R., Quenzel, E. M., Zachau, H. G. and Nahm, M. H. (1991) *J Immunol*, 47, 4007–13.

Tomlinson, I. M. Walter, G., Marks, J. D., Llewelyn, M. B. and Winter, G. (1992) *J.Mol.Biol.*, 227, in press.

TABLE III

Affinities and kinetics of antigen binding by monomeric and dimeric scFv fragments

| scFv | (M/D)[a] | Immobilised species | $k_{on}$[b] (BIAcore) $M^{-1} s^{-1}/10^4$ | $k_{off}$[b] (BIAcore) $s^{-1}/10^{-2}$ | $K_a = k_{on}/k_{off}$ (BIAcore) $M^{-1}/10^6$ | $K_a$ by FQ[c] or inhibition[d] $M^{-1}/10^6$ |
|---|---|---|---|---|---|---|
| αTNF-E7 | D | Human TNFα | 9.0 (±1.2) | 1.4 (0.054) | 6.4 | ND |
| αFOG1-H6 | D | Fog-1 (direct) | 22.2 (±0.4) | 1.8 (0.23) | 12.3 | ND |
| αFOG1-H6 | D | Fog-1 (via RAMIgG1) | 22.1 (±1.9) | 2.4 (0.045) | 9.3 | ND |
| αFOG1-H6 | D | αFOG1-H6 scFv | 104 (±2.4) | ND[e] | ND | ND |
| αFOG1-H6 | M + D | (Measured by inhibition) | ND | ND | ND | 0.3[d] |
| αFOG1-A3 | M + D | (Measured by inhibition) | ND | ND | ND | 0.6[d] |
| αThy-29 | D | Human Thyroglobulin | 6.6 (±1.2) | 0.46 (0.063) | 14.3 | ND |
| αThy-29 | M | Human Thyroglobulin | ND | 2.0 (0.37) | ND | ND |
| αTEL9 | M | Turkey Egg Lysozyme | 39.2 (±2.6) | 1.0 (0.97) | 39.2 | 11.6[e] |

[a] M, monomeric fraction: D, dimeric fraction
[b] Numbers in brackets are standard deviations
[c] FQ, fluorescence quench titration
[d] Calculated from the extent of inhibition of $^{125}$I-Fog-1 binding to the Rh D antigen
[e] Not determined because the dissociation curves were very badly bent

TABLE IV

| Oligonucleotides used | |
|---|---|
| SYNLIB1: | 5'GCC TCC ACC TCT CGA GAC GGT GAC CAG GGT ACC TTG GCC CCA ATA GTC AAA (A/CNN)5 TCT TGC ACA GTA ATA CAC GGC CGT GTC-3' |
| SYNLIB2: | 5'GCC TCC ACC TCT CGA GAC GGT GAC CAG GGT ACC TTG GCC CCA (A/CNN)5 TCT TGC ACA GTA ATA CAC GGC CGT GTC-3' |
| SYNLIB4: | 5'-GAC CAG GGT ACC TTG GCC CCA ((A/C)NN)4 TCT TGC ACA GTA ATA CAC GGC CGT GTC-3' |
| SYNLIB5: | 5'-GAC CAG GGT ACC TTG GCC CCA ((A/C)NN)5 TCT TGC ACA GTA ATA CAC GGC CGT GTC-3' |
| SYNLIB6: | 5'-GAC CAG GGT ACC TTG GCC CCA ((A/C)NN)6 TCT TGC ACA GTA ATA CAC GGC CGT GTC-3' |
| SYNLIB7: | 5'-GAC CAG GGT ACC TTG GCC CCA ((A/C)NN)7 TCT TGC ACA GTA ATA CAC GGC CGT GTC-3' |
| SYNLIB8: | 5'-GAC CAG GGT ACC TTG GCC CCA ((A/C)NN)8 TCT TGC ACA GTA ATA CAC GGC CGT GTC-3' |
| SYNLIB9: | 5'-GAC CAG GGT ACC TTG GCC CCA ((A/C)NN)9 TCT TGC ACA GTA ATA CAC GGC CGT GTC-3' |
| SYNLIB10: | 5'-GAC CAG GGT ACC TTG GCC CCA ((A/C)NN)10 TCT TGC ACA GTA ATA CAC GGC CGT GTC-3' |
| SYNLIB11: | 5'-GAC CAG GGT ACC TTG GCC CCA ((A/C)NN)11 TCT TGC ACA GTA ATA CAC GGC CGT GTC-3' |
| SYNLIB12: | 5'-GAC CAG GGT ACC TTG GCC CCA ((A/C)NN)12 TCT TGC ACA GTA ATA CAC GGC CGT GTC-3' |
| JHSAL: | 5'-GCC TGA ACC GCC TCC ACC AGT CGA CAC GGT GAC CAG GGT ACC TTG GCC CCA-3' |
| CDRFOR: | 5'-CAG GGT ACC TTG GCC CCA-3' |
| CDRBACK: | 5'-GTG TAT TAC TGT GCA AGA-3' |
| Human VH Back Primers | |
| HuVH1aBACKSfi | 5'-GTC CTC GCA ACT GCG GCC CAG CCG GCC ATG GCC CAG GTC CAG CTG GTG CAG TCT GG-3' |
| HuVH2aBACKSfi | 5'-GTC CTC GCA ACT GCG GCC CAG CCG GCC ATG GCC CAG GTC AAC TTA AGG GAG TCT GG-3' |
| HuVH3aBACKSfi | 5'-GTC CTC GCA ACT GCG GCC CAG CCG GCC ATG GCC GAG GTG CAG CTG GTG GAG TCT GG-3' |
| HuVH4aBACKSfi | 5'-GTC CTC GCA ACT GCG GCC CAG CCG GCC ATG GCC CAG GTG CAG CTG CAG GAG TCG GG-3' |
| HuVH5aBACKSfi | 5'-GTC CTC GCA ACT GCG GCC CAG CCG GCC ATG GCC CAG GTG CAG CTG TTG CAG TCT GC-3' |
| HuVH6aBACKSfi | 5'-GTC CTC GCA ACT GCG GCC CAG CCG GCC ATG GCC CAG GTA CAG CTG CAG CAG TCA GG-3' |

What is claimed is:

1. A method of obtaining one or more human antibody molecules comprising an antigen binding site with binding specificity for a human self antigen, the method comprising:
   (a) providing a library of filamentous bacteriophage, each filamentous bacteriophage displaying at its surface an antibody molecule comprising an antigen binding site, and each filamentous bacteriophage containing nucleic acid encoding a polypeptide chain which is a component part of the antibody molecule displaying at the surface of that filamentous bacteriophage;
   (b) selecting from said library of filamentous phage by binding with said human self antigen, one or more antibody molecules with binding specificity for said human self antigen, wherein said human self antigen is a receptor; and testing an antigen binding site of said one or more antibody molecules with binding specificity for said human self antigen for ability to trigger the receptor, whereby one or more antibody molecules which bind to and trigger the receptor are obtained.

2. A method according to claim 1 wherein said antibody molecules displayed at the surface of filamentous bacteriophage are scFv human antibody fragments.

3. A method according to claim 1 wherein said antibody molecules displayed at the surface of filamentous bacteriophage are Fab human antibody fragments.

4. A method according to claim 1 wherein antibody molecules selected in (b) displayed at the surface of filamentous bacteriophage are selected or screened to provide an individual filamentous bacteriophage displaying an antibody molecule or a mixed population of said filamentous bacteriophage with each filamentous bacteriophage containing nucleic acid encoding the antibody molecule or a polypeptide chain thereof which is displayed at its surface.

5. A method according to claim 4 further comprising expressing an antibody molecule or a fragment or derivative thereof in a recombinant host cell from nucleic acid which encodes a selected or screened antibody molecule and which is derived from a filamentous bacteriophage which displays at its surface a selected or screened antibody molecule.

6. A method according to claim 4 further comprising taking nucleic acid from one or more filamentous bacteriophage and providing encoding nucleic acid in a further method to obtain an individual antibody molecule or a mixed population of antibody molecules, or nucleic acid encoding a said individual antibody molecule or a said mixed population of antibody molecules.

7. A method according to claim 5 wherein an expression end product is modified to produce a derivative thereof.

8. A method according to claim 6 wherein an expression end product is modified to produce a derivative thereof.

* * * * *